(12) United States Patent
Wagner et al.

(10) Patent No.: US 8,088,925 B2
(45) Date of Patent: Jan. 3, 2012

(54) HETEROARYL-CARBOXYLIC ACID (SULFAMOYL ALKYL) AMIDE-DERIVATIVES AS FACTOR XA INHIBITORS

(75) Inventors: Michael Wagner, Frankfurt am Main (DE); Matthias Urmann, Frankfurt am Main (DE); Volkmar Wehner, Frankfurt am Main (DE); Martin Lorenz, Frankfurt am Main (DE); Armin Bauer, Frankfurt am Main (DE); Marc Nazare, Frankfurt am Main (DE); Hans Matter, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 457 days.

(21) Appl. No.: 11/940,654

(22) Filed: Nov. 15, 2007

(65) Prior Publication Data

US 2008/0167346 A1    Jul. 10, 2008

Related U.S. Application Data

(63) Continuation of application No. PCT/EP2006/004255, filed on May 6, 2006.

(30) Foreign Application Priority Data

May 20, 2005   (EP) ..................... 05010929

(51) Int. Cl.
| C07D 401/02 | (2006.01) |
|---|---|
| C07D 403/02 | (2006.01) |
| C07D 333/10 | (2006.01) |
| C07D 333/28 | (2006.01) |
| A61K 31/4535 | (2006.01) |
| A61K 31/381 | (2006.01) |
| A61K 31/497 | (2006.01) |

(52) U.S. Cl. .............. 546/207; 546/281.4; 544/359; 544/111; 544/121; 544/129; 549/29; 549/64; 549/65; 514/252.13; 514/438; 514/444; 514/326

(58) Field of Classification Search ............. 546/281.4, 546/207; 514/326, 252.13, 438, 444; 549/29, 549/64, 65; 544/359, 111, 121, 129
See application file for complete search history.

(56) References Cited

U.S. PATENT DOCUMENTS

| 2004/0224978 A1 | 11/2004 | Dai et al. |
|---|---|---|
| 2005/0085518 A1 | 4/2005 | Dai et al. |
| 2005/0096309 A1 | 5/2005 | Han et al. |
| 2006/0052376 A1 | 3/2006 | Dorsch et al. |
| 2007/0066615 A1 | 3/2007 | Gerdes et al. |

FOREIGN PATENT DOCUMENTS

| EP | 1479678 | 11/2004 |
|---|---|---|
| WO | WO 0196303 | 12/2001 |
| WO | 2004/058709 A1 | 7/2004 |

*Primary Examiner* — Rita Desai
(74) *Attorney, Agent, or Firm* — Ronald G. Ort, Esq.; Scully, Scott, Murphy & Presser, P.C.

(57) ABSTRACT

The present invention relates to compounds of the formula I,

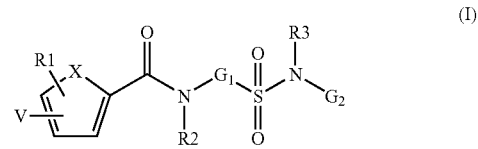

(I)

which exhibit a strong antithrombotic effect and are suitable, for example, for the therapy and prophylaxis of cardiovascular disorders like thromboembolic diseases or restenoses.

3 Claims, No Drawings

HETEROARYL-CARBOXYLIC ACID (SULFAMOYL ALKYL) AMIDE-DERIVATIVES AS FACTOR XA INHIBITORS

The present invention relates to compounds of the formula I,

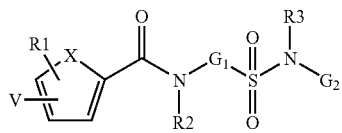

in which R1; R2; R3; V; G1 and G2 have the meanings indicated below. The compounds of the formula I are valuable pharmacologically active compounds. They exhibit a strong anti-thrombotic effect and are suitable, for example, for the therapy and prophylaxis of cardiovascular disorders like thromboembolic diseases or restenoses. They are reversible inhibitors of the blood clotting enzymes factor Xa (FXa) and can in general be applied in conditions in which an undesired activity of factor Xa is present or for the cure or prevention of which an inhibition of factor Xa is intended. The invention furthermore relates to processes for the preparation of compounds of the formula I, their use, in particular as active ingredients in pharmaceuticals, and pharmaceutical preparations comprising them.

Normal haemeostasis is the result of a complex balance between the processes of clot initiation, formation and clot dissolution. The complex interactions between blood cells, specific plasma proteins and the vascular surface maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa activity. It is now believed that inhibitors of factor Xa carry a lower bleeding risk than thrombin inhibitors (A. E. P. Adang & J. B. M. Rewinkel, Drugs of the Future 2000, 25, 369-383).

Low molecular weight, factor Xa-specific blood clotting inhibitors that are effective but do not cause unwanted side effects have been described, for example, in WO-A-95/29189.

However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

The present invention satisfies the above needs by providing novel compounds of the formula I, which exhibit better factor Xa inhibitory activity and are favorable agents with high bioavailability.

Thus, the present invention relates to compounds of the formula I,

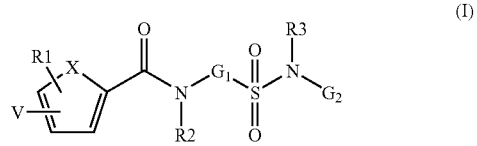

wherein
R1 is halogen, methyl or ethynyl,
X is sulfur, nitrogen, oxygen or the residues —CH═CH— or —CH═N—,
V is hydrogen atom or one or two times halogen or —($C_1$-$C_4$)-alkyl, wherein alkyl is unsubstituted or substituted one, two or three times by R8,
R2 and R3 are independent of one another are identical or different and are a hydrogen atom,
—($C_0$-$C_3$)-alkylene-C(O)—NH—R6,   —($C_0$-$C_3$)-alkylene-C(O)—N(R21)-R22, —($C_0$-$C_3$)-alkylene-C(O)—R10,
—($C_0$-$C_3$)-alkylene-C(O)—O—R10,   —($C_1$-$C_3$)-alkylene-S(O)—R10, —($C_1$-$C_3$)-alkylene-S(O)$_2$—R10,
—($C_1$-$C_5$)-alkylene-S(O)$_2$—N(R4)-R5,   —($C_1$-$C_3$)-alkylene-O—($C_1$-$C_4$)-alkyl,
—($C_0$-$C_5$)-alkylene-($C_1$-$C_3$)-perfluoroalkyl,   —($C_0$-$C_5$)-alkylene-($C_3$-$C_8$)-cycloalkyl-R23,
—($C_1$-$C_4$)-alkyl, wherein alkyl is unsubstituted or substituted one, two or three times by R8,
—($C_0$-$C_4$)-alkylene-aryl, wherein aryl is selected out of the group phenyl, naphthyl, biphenylyl, 2-biphenylyl, 3-biphenylyl, 4-biphenylyl, anthryl or fluorenyl, wherein aryl is mono-, di- or trisubstituted independently of one another by R7, or
—($C_0$-$C_4$)-alkylene-heterocyclyl, wherein heterocyclyl is as defined below and is unsubstituted or mono-, di- or trisubstituted independently of one another by R8,
R4 and R5 are independent of one another are identical or different and are hydrogen atom or —($C_1$-$C_4$)-alkyl,
R6 is 1) a heterocyclyl selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R7 or 2) a 6- to 14-membered aryl selected out of the group phenyl, naphthyl, biphenylyl, 2-biphenylyl, 3-biphenylyl, 4-biphenylyl, anthryl or fluorenyl, wherein aryl is mono-, di- or trisubstituted independently of one another by R7, R7 is halogen, carbamimidoyl, —NO$_2$, =O, —CF$_3$, —C(O)—O—R10, —CN, —C(O)—NH$_2$, —OH, —NH$_2$, —O—CF$_3$, —C(O)—N(R10)-R20, —N(R10)-R20, —(C$_3$-C$_8$)-cycloalkyl, —O—(C$_1$-C$_8$)-alkyl, wherein alkyl is unsubstituted or mono-, di- or trisubstituted independently of one another by halogen, NH$_2$, —OH or a methoxy residue, or —(C$_1$-C$_8$)-alkyl, wherein alkyl is unsubstituted or mono-, di- or trisubstituted independently of one another by halogen, NH$_2$, —OH or a methoxy residue, or —SO$_2$—CH$_3$ or —SO$_2$—CF$_3$, R8 is halogen, —NO$_2$, —CN, =O, —OH, —CF$_3$, —C(O)—O—R10, —C(O)—N(R21)-R22, —N(R21)-R22, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —(C$_1$-C$_3$)-perfluoroalkyl, —(C$_0$-C$_4$)-alkyl-C(O)—O—C(R9, R1)-O—C(O)—R12, —O—R9, —NH—C(O)—NH—R10, —NH—C(O)—NH—R6, —N(R21)-C(O)—R22, —O—CF$_3$, —(C$_0$-C$_4$)-alkyl-C(O)—O—C(R9,R11)-O—C(O)—O—R12, —NH—C(O)—O—R10, heterocyclyl, wherein heterocyclyl is defined above and is unsubstituted mono-, di- or trisubstituted independently of one another by R7, or a residue from the following list

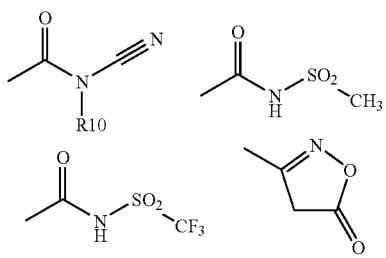

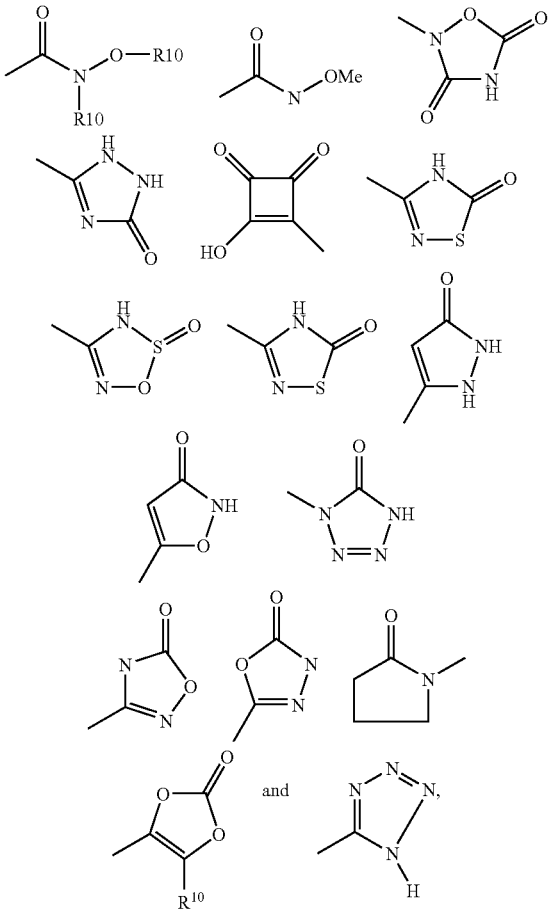

wherein Me is methyl,

R10 and R20 are the same or different and are independently of one another hydrogen, halogen, —(C$_1$-C$_6$)-alkyl, —(C$_0$-C$_4$)-alkyl-OH, —(C$_0$-C$_4$)-alkyl-O—(C$_1$-C$_4$)-alkyl, —(C$_1$-C$_3$)-perfluoroalkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R9 and R11 are the same or different and are independently of one another hydrogen, —(C$_1$-C$_6$)-alkyl, or together with the carbon atom to which they are bonded they can form a 3- to 6 membered carbocyclic ring, which is unsubstituted or substituted one, two or three times by R10, and R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R10, G$_1$ is —(C$_1$-C$_5$)-alkylene or —(C$_3$-C$_8$)-cycloalkyl, wherein methylene is unsubstituted or mono- or disubstituted independently of one another by R13, or —(C$_2$-C$_5$)-alkylene or —(C₃-C₈)-cycloalkyl are unsubstituted or mono- di-, tri- or tetrasubstituted independently of one another by R13, R13 is 1) hydrogen atom,
2) halogen,
3) —(C₁-C₄)-alkyl, wherein alkyl is unsubstituted or mono-, di- or trisubstituted independently of one another by R8,
4) —(C₁-C₃)-perfluoroalkyl,
5) phenyl, wherein phenyl is unsubstituted or mono-, di- or trisubstituted independently of one another by R8,
6) —(C₀-C₄)-alkylene-O—R19, wherein R19 is
  a) hydrogen atom,
  b) —(C₁-C₄)-alkyl, wherein alkyl is unsubstituted or mono-, di- or trisubstituted independently of one another by R8, or
  c) phenyl, wherein phenyl is unsubstituted or mono-, di- or trisubstituted independently of one another by R8,
  d) —CF₃, or
  e) —CHF₂,
  f) heterocyclyl, wherein heterocyclyl is as defined above and is unsubstituted or mono-, di- or trisubstituted independently of one another by R8,
7) —NO₂,
8) —CN,
9) —SO_s—R21, wherein s is 1 or 2,
10) —SO_t—N(R21)-R22, wherein t is 1 or 2,
11) —(C₀-C₄)-alkylene-C(O)—O—R21,
12) —(C₀-C₄)-alkylene-C(O)—N(R21)-R22,
13) —(C₀-C₄)-alkylene-N(R21)-R22,
14) —NR21-SO₂—R22,
15) —S—R10,
16) —(C₀-C₂)alkylene-C(O)—O—(C₂-C₄)-alkylene-O—C(O)—(C₁-C₄)-alkyl,
17) —C(O)—O—C(R9,R11)-O—C(O)—R12,
18) —(C₀-C₂)alkylene-C(O)—O—(C₂-C₄)-alkylene-O—C(O)—O—(C₁-C₆)-alkyl,
19) —C(O)—O—C(R9,R11)-O—C(O)—O—R12,
20) —(C₀-C₄)-alkylene-(C₆-C₁₄)-aryl, wherein aryl is as defined above and alkylene and aryl are independently of one another unsubstituted or mono-, di- or trisubstituted by R8,
21) —(C₀-C₄)-alkylene-heterocyclyl, wherein heterocyclyl is as defined above and alkylene and heterocyclyl are independently of one another unsubstituted or mono-, di- or trisubstituted by R8,
22) —(C₀-C₄)-alkylene-(C₃-C₈)-cycloalkyl, wherein alkylene and cycloalkyl are independently of one another unsubstituted or mono-, di- or trisubstituted by R8,
23) —(C₁-C₄)-alkylene-heterocyclyl, wherein heterocyclyl is as defined above and is unsubstituted or mono-, di- or trisubstituted independently of one another by R8,
24) —(C₀-C₄)-alkylene-O—CH₂—(C₁-C₃)-perfluoroalkylene-CH₂—O—(C₀-C₄)-alkyl,
25) —SO_w—N(R21)-R8, wherein w is 1 or 2,
26) —(C₀-C₄)-alkylene-N(R21)-C(O)—R22,
27) —(C₀-C₄)-alkylene-N(R21)-C(O)—O—R22 or
28) a residue from the following list wherein Me is methyl, or
if two —OR19 residues are attached to adjacent atoms they can form together with the atoms which they are attached to a 5- or 6-membered ring, which is unsubstituted or substituted one, two, three or four times by R8, or
if two R13 are attached to the same carbon atom they can form together a 3- to 8-membered carbocyclic ring, which is unsubstituted or substituted one, two or three times by R10, or
if two R13 are attached to the same carbon atom they can form together a 3- to 8-membered heterocyclic ring, which is unsubstituted or substituted one, two or three times by R10, or
R13 and R3 together with the atoms to which they are bonded form a 5- to 7-membered cyclic group, wherein one of the carbon atoms within said cyclic group can be replaced by nitrogen, oxygen or sulphur and wherein said cyclic group is unsubstituted or substituted one, two or three times by R7,
R21 and R22 are the same or different and are independently of one another
1) hydrogen atom,
2) —(C₁-C₆)-alkyl, wherein alkyl is unsubstituted or mono-, di- or trisubstituted independently of one another by R7, 3) —(C$_0$-C$_6$)-alkylene-(C$_3$-C$_8$)-cycloalkyl,
4) —SO$_t$—R10, wherein t is 1 or 2,
5) —(C$_0$-C$_6$)-alkylene-(C$_6$-C$_{14}$)-aryl, wherein aryl is as defined above and alkylene and aryl independently from one another are unsubstituted or mono-, di- or trisubstituted by R7,
6) —(C$_1$-C$_3$)-perfluoroalkyl,
7) —O—R12 or
8) —(C$_0$-C$_6$)-alkylene-heterocyclyl, wherein heterocyclyl is as defined above and alkylene and heterocyclyl independently from one another are unsubstituted or mono-, di- or trisubstituted by R7, or R21 and R22 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen, wherein said heterocyclic ring is unsubstituted or mono-, di- or trisubstituted independently of one another by R7, R23 is hydrogen atom, —OH or —O—(C$_1$-C$_4$)-alkyl, G$_2$ is azetidine, pyrrolidine, piperidine, azepane, hexahydro-pyridazine, hexahydro-pyrimidine, piperazine, [1,2]diazepane, [1,3]diazepane or [1,4]diazepane, wherein G2 is unsubstituted or mono-, di-, tri or tetrasubstituted independently of one another by M or Y, M is —(C$_1$-C$_6$)-alkyl, —(C$_2$-C$_6$)-alkenyl, —(C$_2$-C$_6$)-alkinyl, —(C$_3$-C$_6$)-cycloalkyl, —(C$_0$-C$_2$)-alkylene-aryl, wherein aryl is as defined above, —(C$_1$-C$_4$)-alkyl-(C$_3$-C$_6$)-cycloalkyl, pyridyl or piperidinyl, wherein piperidinyl is unsubstituted or substituted by —(C$_1$-C$_6$)-alkyl, Y is hydrogen atom, halogen, =O, —OH, —CF$_3$, —C(O)—O—R10, —C(O)—N(R10)-R20, —N(R10)-R20, —(C$_3$-C$_8$)-cycloalkyl, —(C$_0$-C$_3$)-alkylene-O—R10, phenyl, —(C$_1$-C$_8$)-alkyl, —(C$_1$-C$_8$)-alkoxy, —(C$_0$-C$_4$)-alkyl-C(O)—O—C(R9,R11)-O—C(O)—R12, —O—R9, —O—CF$_3$, —(C$_1$-C$_3$)-perfluoroalkyl, or —(C$_0$-C$_4$)-alkyl-C(O)—O—C(R9,R11)-O—C(O)—O—R12, in all its stereoisomeric forms and mixtures thereof in any ratio, and its physiologically tolerable salts.

2) The present invention also relates to compounds of the formula I, wherein

X is sulfur, nitrogen, oxygen or the residues —CH=CH— or —CH=N—,

V is hydrogen atom, R1 is chlorine, bromine or methyl,

R2 and R3 are independent of one another are identical or different and are a hydrogen atom,
—(C$_0$-C$_3$)-alkylene-C(O)—NH—R6, —(C$_0$-C$_3$)-alkylene-C(O)—N(R21)-R22, —(C$_0$-C$_3$)-alkylene-C(O)—R10,
—(C$_0$-C$_3$)-alkylene-C(O)—O—R10, —(C$_1$-C$_3$)-alkylene-S(O)—R10, —(C$_1$-C$_3$)-alkylene-S(O)$_2$—R10,
—(C$_1$-C$_5$)-alkylene-S(O)$_2$—N(R4)-R5, —(C$_1$-C$_3$)-alkylene-O—(C$_1$-C$_4$)-alkyl,
—(C$_0$-C$_5$)-alkylene-(C$_1$-C$_3$)-perfluoroalkyl, —(C$_0$-C$_5$)-alkylene-(C$_3$-C$_8$)-cycloalkyl-R23,
—(C$_1$-C$_4$)-alkyl, wherein alkyl is unsubstituted or substituted one, two or three times by R8,
—(C$_0$-C$_4$)-alkylene-aryl, wherein aryl is selected out of the group phenyl, naphthyl, biphenylyl, anthryl or fluorenyl, wherein aryl is mono-, di- or trisubstituted independently of one another by R7, or
—(C$_0$-C$_4$)-alkylene-heterocyclyl, wherein heterocyclyl is as defined below and is unsubstituted or mono-, di- or trisubstituted independently of one another by R8, R4 and R5 are independent of one another are identical or different and are hydrogen atom or —(C$_1$-C$_4$)-alkyl, R6 is 1) a heterocyclyl selected out of the group azabenzimidazolyl, azepinyl, azetidinyl, benzimidazolyl, benzisoxazolyl, benzisothiazolyl, 1,3-benzodioxolyl, benzofuranyl, benzoxazolyl, benzothiazolyl, benzothiophenyl, cinnolinyl, chromanyl, furanyl, imidazolyl, indanyl, 1H-indazolyl, indolyl, isochromanyl, isoindolyl, isoquinolinyl, isothiazolyl, isoxazolyl, ketopiperazinyl, morholinyl, naphthyridinyl, oxadiazolyl, oxazolyl, phenylpyridyl, phthalazinyl, piperazinyl, piperidinyl, pteridinyl, purinyl, pyrazinyl, pyrazolyl, pyridazinyl, pyridyl, pyridoimidazolyl, pyridooxazolyl, pyridopyrimidinyl, pyridothienyl, pyrimidinyl, pyrrolidinyl, pyrrolidinonyl, pyrrolyl, quinazolinyl, quinolinyl, quinolyl, quinoxalinyl, tetrahydroisoquinolinyl, tetrahydropyranyl, 1,4,5,6-tetrahydropyridazinyl, tetrazolyl, thiazolyl, thiadiazolyl, thienyl, thiomorpholinyl or triazolyl, wherein said heterocyclyl is unsubstituted or mono-, di- or trisubstituted independently of one another by R7 or 2) a 6- to 14-membered aryl selected out of the group phenyl, naphthyl, biphenylyl, anthryl or fluorenyl, wherein aryl is mono-, di- or trisubstituted independently of one another by R7, R7 is halogen, carbamimidoyl, —NO$_2$, =O, —CF$_3$, —C(O)—O—R10, —CN, —C(O)—NH$_2$, —OH, —NH$_2$, —O—CF$_3$,
—C(O)—N(R10)-R20, —N(R10)-R20, —(C$_3$-C$_8$)-cycloalkyl, —O—(C$_1$-C$_8$)-alkyl, wherein alkyl is unsubstituted or mono-, di- or trisubstituted independently of one another by halogen, NH$_2$, —OH or a methoxy residue, or —(C$_1$-C$_8$)-alkyl, wherein alkyl is unsubstituted or mono-, di- or trisubstituted independently of one another by halogen, NH$_2$, —OH or a methoxy residue, or —SO$_2$—CH$_3$ or —SO$_2$—CF$_3$, R8 is halogen, —NO$_2$, —CN, =O, —OH, —CF$_3$, —C(O)—O—R10, —C(O)—N(R21)-R22, —N(R21)-R22, —O—CF$_3$,
—(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10,
—(C$_1$-C$_8$)-alkyl, —(C$_1$-C$_8$)-alkoxy, phenyl, phenyloxy-, —(C$_1$-C$_3$)-perfluoroalkyl, —O—R9,
—NH—C(O)—NH—R10, —NH—C(O)—NH—R6, —N(R21)-C(O)—R22, —(C$_0$-C$_4$)-alkyl-C(O)—O—C(R9,R11)-O—C(O)—R12, —(C$_0$-C$_4$)-alkyl-C(O)—O—C(R9,R11)-O—C(O)—O—R12, —NH—C(O)—O—R10, heterocyclyl, wherein heterocyclyl is defined above and is unsubstituted mono-, di- or trisubstituted independently of one another by R7, or a residue from the following list

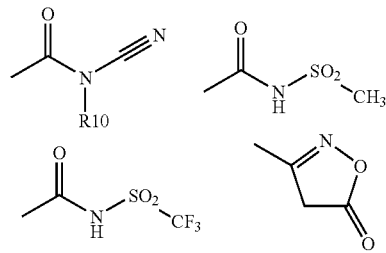

-continued

[chemical structures]

wherein Me is methyl,

R10 and R20 are the same or different and are independently of one another hydrogen, halogen, —($C_1$-$C_6$)-alkyl, —($C_0$-$C_4$)-alkyl-OH, —($C_0$-$C_4$)-alkyl-O—($C_1$-$C_4$)-alkyl, —($C_1$-$C_3$)-perfluoroalkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R9 and R11 are the same or different and are independently of one another hydrogen,
—($C_1$-$C_6$)-alkyl, or together with the carbon atom to which they are bonded they form a cyclopropyl, cyclobutyl, cyclopentyl or cyclohexyl ring, which is unsubstituted or substituted one, two or three times by R10, and R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl,
—($C_1$-$C_6$)-alkyl-O—($C_1$-$C_8$)-alkyl-($C_3$-$C_8$)-cycloalkyl,
—($C_1$-$C_6$)-alkyl-($C_3$-$C_8$)-cycloalkyl, wherein said cycloalkyl ring is unsubstituted or substituted one, two or three times by —OH,
—O—($C_1$-$C_4$)-alkyl or R10, $G_1$ is —($C_2$-$C_4$)-alkylene or —($C_3$-$C_6$)-cycloalkyl, wherein —($C_2$-$C_4$)-alkylene or —($C_3$-$C_6$)-cycloalkyl are unsubstituted or mono- di-, tri- or tetrasubstituted independently of one another by R13, R13 is 1) hydrogen atom,
2) halogen,
3) —($C_1$-$C_4$)-alkyl, wherein alkyl is unsubstituted or mono-, di- or trisubstituted independently of one another by R8,
4) —($C_1$-$C_3$)-perfluoroalkyl,
5) phenyl, wherein phenyl is unsubstituted or mono-, di- or trisubstituted independently of one another by R8,
6) —($C_0$-$C_4$)-alkylene-O—R19, wherein R19 is
   a) hydrogen atom,
   b) —($C_1$-$C_4$)-alkyl, wherein alkyl is unsubstituted or mono-, di- or trisubstituted independently of one another by R8, or
   c) phenyl, wherein phenyl is unsubstituted or mono-, di- or trisubstituted independently of one another by R8,
   d) —$CF_3$, or
   e) —$CHF_2$,
   f) heterocyclyl, wherein heterocyclyl is as defined above and is unsubstituted or mono-, di- or trisubstituted independently of one another by R8,
7) —$NO_2$,
8) —CN,
9) -$SO_s$—R21, wherein s is 1 or 2,
10) —$SO_t$—N(R21)-R22, wherein t is 1 or 2,
11) —($C_0$-$C_4$)-alkylene-C(O)—O—R21,
12) —($C_0$-$C_4$)-alkylene-C(O)—N(R21)-R22,
13) —($C_0$-$C_4$)-alkylene-N(R21)-R22,
14) —NR21-$SO_2$—R22,
15) —S—R10,
16) —($C_0$-$C_2$)alkylene-C(O)—O—($C_2$-$C_4$)-alkylene-O—C(O)—($C_1$-$C_4$)-alkyl,
17) —C(O)—O—C(R9,R11)-O—C(O)—R12,
18) —($C_0$-$C_2$)alkylene-C(O)—O—($C_2$-$C_4$)-alkylene-O—C(O)—O—($C_1$-$C_6$)-alkyl,
19) —C(O)—O—C(R9,R11)-O—C(O)—O—R12,
20) —($C_0$-$C_4$)-alkylene-($C_6$-$C_{14}$)-aryl, wherein aryl is as defined above and alkylene and aryl are independently of one another unsubstituted or mono-, di- or trisubstituted by R8,
21) —($C_0$-$C_4$)-alkylene-heterocyclyl, wherein heterocyclyl is as defined above and alkylene and heterocyclyl are independently of one another unsubstituted or mono-, di- or trisubstituted by R8,
22) —($C_0$-$C_4$)-alkylene-($C_3$-$C_6$)-cycloalkyl, wherein alkylene and cycloalkyl are independently of one another unsubstituted or mono-, di- or trisubstituted by R8,
23) —($C_1$-$C_4$)-alkylene-heterocyclyl, wherein heterocyclyl is as defined above and is unsubstituted or mono-, di- or trisubstituted independently of one another by R8,
24) —($C_0$-$C_4$)-alkylene-O—$CH_2$—($C_1$-$C_3$)-perfluoroalkylene-$CH_2$—O—($C_0$-$C_4$)-alkyl,
25) —$SO_w$—N(R21)-R8, wherein w is 1 or 2,
26) —($C_0$-$C_4$)-alkylene-N(R21)-C(O)—R22,
27) —($C_0$-$C_4$)-alkylene-N(R21)-C(O)—O—R22 or
28) a residue from the following list

[chemical structures]

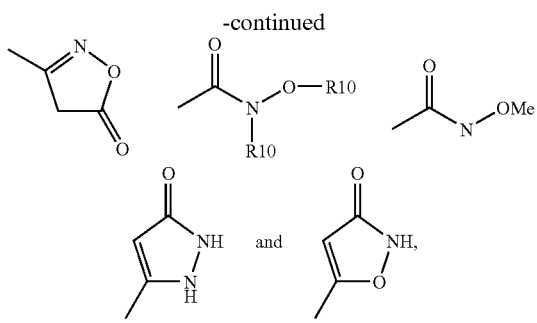

wherein Me is methyl, or if two —OR19 residues are attached to adjacent atoms they can form together with the atoms which they are attached to a 1,3-dioxolane ring or a 2,3-dihydro-[1,4]dioxine ring, which is substituted one, two, three or four times by R8, or if two R13 are attached to the same carbon atom they can form together a 3- to 8-membered carbocyclic ring, which is unsubstituted or substituted one, two or three times by R10, or if two R13 are attached to the same carbon atom they can form together a 3- to 8-membered heterocyclic ring, which is unsubstituted or substituted one, two or three times by R10, or R13 and R3 together with the atoms to which they are bonded form a 5- to 7-membered cyclic group, wherein one of the carbon atoms within said cyclic group can be selected from nitrogen, oxygen or sulphur selected out of the group isothiazolidine 1,1-dioxide; 2,5-dihydro-isothiazole 1,1-dioxide; 2,3-dihydro-isothiazole 1,1-dioxide; [1,2]thiazinane 1,1-dioxide; 2H-[1,2]thiazine 1,1-dioxide; 5,6-dihydro-2H-[1,2]thiazine 1,1-dioxide; 3,4-dihydro-2H-[1,2]thiazine 1,1-dioxide; 3,6-dihydro-2H-[1,2]thiazine 1,1-dioxide; [1,2]thiazepane 1,1-dioxide; 2,5,6,7-tetrahydro-[1,2]thiazepine 1,1-dioxide; 2,7-dihydro-[1,2]thiazepine 1,1-dioxide; 2,5-dihydro-[1,2]thiazepine 1,1-dioxide; [1,2,4]thiadiazolidine 1,1-dioxide; [1,2,3]thiadiazolidine 1,1-dioxide; 2,5-dihydro-[1,2,4]thiadiazole 1,1-dioxide; [1,3,4]oxathiazolidine 3,3-dioxide; [1,3,2]oxathiazo-lidine 3,3-dioxide; [1,4,2]dithiazolidine 1,1-dioxide; [1,3,2] dithiazolidine 1,1-dioxide; [1,2,5]thiadiazinane 1,1-dioxide; [1,3,4]oxathiazinane 3,3-dioxide; [1,4,3] oxathiazinane 4,4-dioxide; [1,5,2]dithiazinane 1,1-dioxide; [1,2,6]thiadiazepane 1,1-dioxide; [1,3,4] oxathiazepane 3,3-dioxide or [1,6,2]dithiazepane 1,1-dioxide and wherein said cyclic group is unsubstituted or substituted one, two or three times by R7, R21 and R22 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_6$)-cycloalkyl,
4) —$SO_t$—R10, wherein t is 1 or 2,
5) —($C_0$-$C_6$)-alkylene-($C_6$-$C_{14}$)-aryl, wherein aryl is as defined above and alkylene and aryl independently from one another are unsubstituted or mono-, di- or trisubstituted by R7,
6) —($C_1$-$C_3$)-perfluoroalkyl,
7) —O—R12 or
8) —($C_0$-$C_6$)-alkylene-heterocyclyl, wherein heterocyclyl is as defined above and alkylene and heterocyclyl independently from one another are unsubstituted or mono-, di- or trisubstituted by R7, or R21 and R22 together with the nitrogen atom to which they are bonded can form a heterocyclic ring from the group azepine, azetidine, dioxazole, dioxazine, 1,4-diazepane, 1,2-diazepine, 1,3-diazepine, 1,4-diazepine, imidazole, imidazoline, imidazolidine, isothiazolidine, isothiazoline, isoxazoline, isoxazolidine, 2-isoxazoline, ketomorpholine, ketopiperazine, N-methyl-[1,4]diazepane, N-methylpiperazine, morpholine, [1,4]oxazepane, 1,4-oxazepine, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazolidine, thiazoline, thiomorpholine, 1,2,3-triazine, 1,2,4-triazine, 1,3,5-triazine, 1,2,3-triazole or 1,2,4-triazole, wherein the heterocyclic ring is unsubstituted or mono-, di- or trisubstituted by R7, R23 is hydrogen atom, —OH or —O—($C_1$-$C_4$)-alkyl, $G_2$ is azetidine, pyrrolidine, piperidine, azepane, piperazine, [1,3]diazepane or [1,4]diazepane,
wherein G2 is unsubstituted or mono-, di-, tri- or tetrasubstituted independently of one another by M or Y, M is —($C_1$-$C_6$)-alkyl, —($C_2$-$C_6$)-alkenyl, —($C_2$-$C_6$)-alkinyl, —($C_3$-$C_6$)-cycloalkyl, —($C_0$-$C_2$)-alkylene-aryl, wherein aryl is as defined above, —($C_1$-$C_4$)-alkyl-($C_3$-$C_6$)-cycloalkyl, pyridyl or piperidinyl, wherein piperidinyl is unsubstituted or substituted by —($C_1$-$C_6$)-alkyl, Y is hydrogen atom, halogen, =O, —OH, —$CF_3$, —C(O)—O—R10, —C(O)—N(R10)-R20, —N(R10)-R20, —($C_3$-$C_9$)-cycloalkyl, —($C_0$-$C_3$)-alkylene-O—R10, —($C_1$-$C_8$)-alkyl, —($C_1$-$C_8$)-alkoxy, phenyl, —O—R9, —($C_1$-$C_3$)-perfluoroalkyl, —O—$CF_3$, —($C_0$-$C_4$)-alkylene-C(O)—O—C(R9,R11)-O—C(O)—R12 or —($C_0$-$C_4$)-alkylene-C(O)—O—C(R9,R11)-O—C(O)—O—R12, in all its stereoisomeric forms and mixtures thereof in any ratio, and its physiologically tolerable salts.

3) The present invention also relates to the compounds of the formula I, wherein X is sulfur, oxygen or the residues —CH=CH— or —CH=N—, V is hydrogen atom, R1 is chlorine, bromine or methyl, R2 is hydrogen atom, R3 is a hydrogen atom, —($C_0$-$C_3$)-alkylene-C(O)—NH—R6, —($C_0$-$C_3$)-alkylene-C(O)—N(R21)-R22, ($C_0$-$C_3$)-alkylene-C(O)—R10, —($C_0$-$C_3$)-alkylene-C(O)—O—R10, —($C_1$-$C_3$)-alkylene-S(O)$_2$—($C_1$-$C_4$)-alkyl, —($C_1$-$C_3$)-alkylene-S(O)$_2$-phenyl, —($C_0$-$C_5$)-alkylene-($C_1$-$C_3$)-perfluoroalkyl, —($C_0$-$C_5$)-alkylene-($C_3$-$C_6$)-cycloalkyl-R23, —($C_1$-$C_4$)-alkyl, wherein alkyl is unsubstituted or mono-, di- or trisubstituted independently of one another by R8, —($C_0$-$C_4$)-alkylene-phenyl, wherein phenyl is unsubstituted or mono-, di- or trisubstituted independently of one another by R8 or —($C_0$-$C_4$)-alkylene-heterocyclyl, wherein heterocyclyl is as defined below and is unsubstituted or mono-, di- or trisubstituted independently of one another by R8, R6 is heterocyclyl, wherein heterocyclyl is selected out of the group azabenzimidazolyl, azepinyl, azetidinyl, benzimidazolyl, benzisoxazolyl, benzisothiazolyl, 1,3-benzodioxolyl, benzofuranyl, benzoxazolyl, benzothiazolyl, benzothiophenyl, cinnolinyl, chromanyl, furanyl, imidazolyl, indanyl, 1H-indazolyl, indolyl, isochromanyl, isoindolyl, isoquinolinyl, isothiazolyl, isoxazolyl, ketopiperazinyl, morholinyl, naphthyridinyl, oxadiazolyl, oxazolyl, phenylpyridyl, phthalazinyl, piperazinyl, piperidinyl, pteridinyl, purinyl, pyrazinyl, pyrazolyl, pyridazinyl, pyridyl, pyridoimidazolyl, pyridooxazolyl, pyridopyrimidinyl, pyridothienyl, pyrimidinyl, pyrrolidinyl, pyrrolidinonyl, pyrrolyl, quinazolinyl, quinolinyl, quinolyl, quinoxalinyl, tetrahydroisoquinolinyl, tetrahydropyranyl, 1,4,5,6-tetrahydro-pyridazinyl, tetrazolyl, thiazolyl, thiadiazolyl, thienyl, thiomorpholinyl or triazolyl, and wherein heterocyclyl is independently of one another unsubstituted or mono-, di- or trisubstituted by R7, R7 is halogen, carbamimidoyl, —NO$_2$, =O, —CF$_3$, —C(O)—O—R10, —CN, —C(O)—NH$_2$, —OH, —NH$_2$, —O—CF$_3$, —C(O)—N(R10)-R20, —N(R10)-R20, —(C$_3$-C$_9$)-cycloalkyl, —O—(C$_1$-C$_8$)-alkyl, wherein alkyl is unsubstituted or mono-, di- or trisubstituted independently of one another by halogen, NH$_2$, —OH or a methoxy residue, or —(C$_1$-C$_8$)-alkyl, wherein alkyl is unsubstituted or mono-, di- or trisubstituted independently of one another by halogen, NH$_2$, —OH or a methoxy residue, or —SO$_2$—CH$_3$ or —SO$_2$—CF$_3$, R8 is halogen, =O, —OH, —CF$_3$, —C(O)—O—R10, —C(O)—N(R21)-R22, —N(R21)-R22, —(C$_3$-C$_6$)-cycloalkyl,
—(C$_0$-C$_3$)-alkylene-O—R10, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —(C$_1$-C$_3$)-perfluoroalkyl, —(C$_0$-C$_4$)-alkyl-C(O)—O—C(R9,R11)-O—C(O)—R12,
—O—R9, —NH—C(O)—NH—R10, —N(R21)-C(O)—R22, —(C$_0$-C$_4$)-alkyl-C(O)—O—C(R9, R11)-O—C(O)—O—R12,
—O—CF$_3$, —NH—C(O)—O—R10, or heterocyclyl, wherein heterocyclyl is as defined above and wherein heterocyclyl is independently of one another unsubstituted or mono- or disubstituted by R7, R10 and R20 are the same or different and are independently of one another hydrogen atom, halogen, —(C$_1$-C$_6$)-alkyl, —(C$_0$-C$_4$)-alkyl-OH, —(C$_0$-C$_4$)-alkylene-O—(C$_1$-C$_4$)-alkyl or
—(C$_1$-C$_3$)-perfluoroalkyl or —(C$_0$-C$_5$)-alkylene-(C$_3$-C$_8$)-cycloalkyl, R9 and R11 are the same or different and are independently of one another hydrogen,
—(C$_1$-C$_6$)-alkyl, or together with the carbon atom to which they are bonded they form a cyclopropyl, cyclobutyl, cyclopentyl or cyclohexyl ring, which is unsubstituted or substituted one, two or three times by R10, and R12 is —(C$_1$-C$_6$)-alkyl, —(C$_1$-C$_6$)-alkyl-OH, —(C$_1$-C$_6$)-alkylene-O—(C$_1$-C$_6$)-alkyl, —(C$_3$-C$_6$)-cycloalkyl,
—(C$_1$-C$_6$)-alkylene-O—(C$_1$-C$_8$)-alkylene-(C$_3$-C$_6$)-cycloalkyl, —(C$_1$-C$_6$)-alkylene-(C$_3$-C$_6$)-cycloalkyl, wherein said cycloalkyl ring is unsubstituted or substituted one, two or three times by —OH,
—O—(C$_1$-C$_4$)-alkyl or R10, G$_1$ is —(C$_2$-C$_4$)-alkylene or —(C$_3$-C$_6$)-cycloalkyl, wherein —(C$_2$-C$_4$)-alkylene or —(C$_3$-C$_6$)-cycloalkyl are unsubstituted or mono- di-, tri- or tetrasubstituted independently of one another by R13, R13 is a hydrogen atom, fluorine, —(C$_0$-C$_4$)-alkylene-N(R21)-R22, —(C$_0$-C$_4$)-alkylene-C(O)—N(R21)-R22, —(C$_0$-C$_4$)-alkylene-O—R22, —(C$_0$-C$_4$)-alkylene-OH, —(C$_0$-C$_4$)-alkylene-C(O)—O—R21,
—(C$_0$-C$_4$)-alkylene-N(R21)-C(O)—R22, —(C$_0$-C$_4$)-alkylene-N(R21)-C(O)—O—R22, —(C$_1$-C$_4$)-alkyl, wherein alkyl is unsubstituted or mono-, di- or trisubstituted independently of one another by R8, —(C$_0$-C$_4$)-alkylene-(C$_6$-C$_{14}$)-aryl, wherein —(C$_6$-C$_{14}$)-aryl is selected out of the group phenyl, naphthyl, biphenylyl, anthryl or fluorenyl and alkylene and aryl are independently of one another unsubstituted or mono-, di- or trisubstituted by R8, or
—(C$_0$-C$_4$)-alkylene-heterocyclyl, wherein heterocyclyl is as defined above and alkylene and wherein heterocyclyl are independently of one another unsubstituted or mono-, di- or trisubstituted by R8, if two R13 are attached to the same carbon atom they can form together a 3- to 8-membered carbocyclic ring, which is unsubstituted or substituted one, two or three times by R10, or R13 and R3 together with the atoms to which they are bonded form a isothiazolidine 1,1-dioxide, [1,2]thiazinane 1,1-dioxide or [1,4,3]oxathiazinane 4,4-dioxide group and wherein said group is unsubstituted or substituted one or two times by R7, R21 and R22 are independently of one another identical or different and are
1) hydrogen atom,
2) —(C$_1$-C$_6$)-alkyl, wherein alkyl is unsubstituted or mono-, di- or trisubstituted independently of one another by R7,
3) —(C$_0$-C$_3$)-alkylene-heterocyclyl, wherein heterocyclyl is unsubstituted or mono-, di- or trisubstituted by R7,
4) —(C$_0$-C$_3$)-alkylene-(C$_3$-C$_6$)-cycloalkyl,
5) —(C$_1$-C$_3$)-perfluoroalkyl, or
6) —(C$_0$-C$_6$)-alkylene-phenyl, wherein phenyl is as defined above and wherein alkyl and phenyl are independently from one another unsubstituted or mono-, di- or trisubstituted by R7, R21 and R22 together with the nitrogen atom to which they are bonded can form a heterocyclic ring from the group azepine, azetidine, 1,4-diazepane, 1,3-diazepine, 1,4-diazepine, imidazole, isothiazoline, isoxazoline, isoxazolidine, 2-isoxazoline, ketomorpholine, ketopiperazine, N-methyl-[1,4]diazepane, N-methyl-piperazine, morpholine, [1,4]oxazepane, 1,4-oxazepine, piperazine, piperidine, pyrazole, pyrazoline, pyrazolidine, pyrrole, pyrrolidine, pyrrolidinone, pyrroline, tetrahydropyridine, tetrazole, thiazolidine, thiazoline, thiomorpholine, 1,2,3-triazole or 1,2,4-triazole, R23 is hydrogen atom, —OH or —O—(C$_1$-C$_4$)-alkyl, G$_2$ is azetidine, piperazine or piperidine,
wherein G2 is unsubstituted or mono-, di- or trisubstituted independently of one another by M, and M is —(C$_1$-C$_6$)-alkyl, cyclopropyl, benzyl or pyridyl,
in all its stereoisomeric forms and mixtures thereof in any ratio, and its physiologically tolerable salts.

4) The present invention also relates to the compounds of the formula Ia, wherein

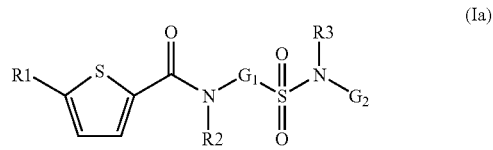

R1 is chlorine, bromine or methyl,
R2 is hydrogen atom,
R3 is a hydrogen atom, —(C$_0$-C$_3$)-alkylene-C(O)—NH—R6, —(C$_0$-C$_3$)-alkylene-C(O)—N(R21)-R22,
—(C$_0$-C$_3$)-alkylene-C(O)—R10, —(C$_0$-C$_3$)-alkylene-C(O)—O—R10, —(C$_1$-C$_3$)-alkylene-S(O)$_2$-phenyl, —($C_0$-$C_5$)-alkylene-($C_1$-$C_3$)-perfluoroalkyl, —($C_0$-$C_5$)-alkylene-($C_3$-$C_6$)-cycloalkyl,
—($C_1$-$C_4$)-alkyl, wherein alkyl is unsubstituted or mono-, di- or trisubstituted independently of one another by R8,
—($C_0$-$C_4$)-alkylene-phenyl, wherein phenyl is unsubstituted or mono-, di- or trisubstituted independently of one another by R8, or —($C_0$-$C_4$)-alkylene-heterocyclyl, wherein heterocyclyl is as defined below and is unsubstituted or mono-, di or trisubstituted independently of one another by R8, R6 is heterocyclyl, wherein heterocyclyl is selected out of the group azabenzimidazolyl, azepinyl, azetidinyl, benzimidazolyl, benzisoxazolyl, benzisothiazolyl, 1,3-benzodioxolyl, benzofuranyl, benzoxazolyl, benzothiazolyl, benzothiophenyl, cinnolinyl, chromanyl, furanyl, imidazolyl, indanyl, 1H-indazolyl, indolyl, isochromanyl, isoindolyl, isoquinolinyl, isothiazolyl, isoxazolyl, ketopiperazinyl, morpholinyl, naphthyridinyl, oxadiazolyl, oxazolyl, phenylpyridyl, phthalazinyl, piperazinyl, piperidinyl, pteridinyl, purinyl, pyrazinyl, pyrazolyl, pyridazinyl, pyridyl, pyridoimidazolyl, pyridooxazolyl, pyridopyrimidinyl, pyridothienyl, pyrimidinyl, pyrrolidinyl, pyrrolidinonyl, pyrrolyl, quinazolinyl, quinolinyl, quinolyl, quinoxalinyl, tetrahydroisoquinolinyl, tetrahydropyranyl, 1,4,5,6-tetrahydro-pyridazinyl, tetrazolyl, thiazolyl, thiadiazolyl, thienyl, thiomorpholinyl or triazolyl, and wherein heterocyclyl is independently of one another unsubstituted or mono-, di- or trisubstituted by R7, R7 is halogen, =O, —$CF_3$, —C(O)—O—R10, —CN, —C(O)—$NH_2$, —OH, —$NH_2$, —O—$CF_3$, —C(O)—N(R10)-R20, —N(R10)-R20, —($C_3$-$C_8$)-cycloalkyl, —O—($C_1$-$C_8$)-alkyl, wherein alkyl is unsubstituted or mono-, di- or trisubstituted independently of one another by halogen, $NH_2$, —OH or a methoxy residue, or —($C_1$-$C_8$)-alkyl, wherein alkyl is unsubstituted or mono-, di- or trisubstituted independently of one another by halogen, $NH_2$, —OH or a methoxy residue, R8 is halogen, =O, —OH, —$CF_3$, —C(O)—O—R10, —C(O)—N(R21)-R22, —N(R21)-R22, —($C_3$-$C_6$)-cycloalkyl,
—($C_0$-$C_3$)-alkylene-O—R10, —($C_1$-$C_6$)-alkyl, —($C_1$-$C_8$)-alkoxy, phenyl, phenyloxy-, —($C_1$-$C_3$)-perfluoroalkyl, or heterocyclyl, wherein heterocyclyl is as defined above and wherein heterocyclyl is independently of one another unsubstituted or mono- or disubstituted by R7, $G_1$ is —($C_2$-$C_4$)-alkylene, wherein —($C_2$-$C_4$)-alkylene is unsubstituted or mono- or disubstituted independently of one another by R13, R13 is a hydrogen atom, fluorine, —($C_0$-$C_4$)-alkylene-N(R21)-R22, —($C_0$-$C_4$)-alkylene-C(O)—N(R21)-R22, —($C_0$-$C_2$)-alkylene-O—R22, —($C_0$-$C_4$)-alkylene-OH, —($C_0$-$C_4$)-alkylene-C(O)—O—R21, or —($C_1$-$C_4$)-alkyl, R13 and R3 together with the atoms to which they are bonded form a isothiazolidine 1,1-dioxide, [1,2]thiazinane 1,1-dioxide or [1,4,3]oxathiazinane 4,4-dioxide group and wherein said group is unsubstituted or substituted one time by R7, R21 and R22 are independently of one another identical or different and are
1) hydrogen atom,
2) —($C_1$-$C_6$)-alkyl, wherein alkyl is unsubstituted or mono-, di- or trisubstituted independently of one another by R7,
3) —($C_0$-$C_3$)-alkylene-($C_3$-$C_6$)-cycloalkyl,
4) —($C_1$-$C_3$)-perfluoroalkyl, or
5) —($C_0$-$C_6$)-alkylene-phenyl, wherein phenyl is as defined above and wherein alkylene and phenyl are independently from one another unsubstituted or mono-, di- or trisubstituted by R7, or R21 and R22 together with the nitrogen atom to which they are bonded can form a heterocyclic ring from the group N-methyl-piperazine or morpholine, R10 and R20 are the same or different and are independently of one another hydrogen atom, halogen, —($C_1$-$C_6$)-alkyl, —($C_0$-$C_4$)-alkyl-OH, —($C_0$-$C_4$)-alkylene-O—($C_1$-$C_4$)-alkyl,
—($C_1$-$C_3$)-perfluoroalkyl or —($C_0$-$C_3$)-alkylene-($C_3$-$C_8$)-cycloalkyl, R9 and R11 are the same or different and are independently of one another hydrogen,
—($C_1$-$C_6$)-alkyl, or together with the carbon atom to which they are bonded they form a cyclopropyl, cyclobutyl, cyclopentyl or cyclohexyl ring, which is unsubstituted or substituted one, two or three times by R10, and R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_6$)-cycloalkyl,
—($C_1$-$C_6$)-alkylene-O—($C_1$-$C_8$)-alkyl-($C_3$-$C_6$)-cycloalkyl, —($C_1$-$C_6$)-alkylene-($C_3$-$C_6$)-cycloalkyl, wherein said cycloalkyl ring is unsubstituted or substituted one, two or three times by —OH,
—O—($C_1$-$C_4$)-alkyl or R10, $G_2$ is azetidine, piperazine or piperidine,
wherein G2 is unsubstituted or monosubstituted by isopropyl, cyclopropyl, benzyl or pyridyl, in all its stereoisomeric forms and mixtures thereof in any ratio, and its physiologically tolerable salts.

5) The present invention also relates to the compounds of the formula Ia, wherein
R1 is bromine, methyl or chlorine,
R2 is hydrogen atom,
R3 is a hydrogen atom, —($C_0$-$C_1$)-alkylene-C(O)—NH—R6, —($C_0$-$C_1$)-alkylene-C(O)—N(R21)-R22,
—($C_0$-$C_2$)-alkylene-C(O)—R10, —($C_0$-$C_1$)-alkylene-($C_1$-$C_2$)-perfluoroalkyl, —($C_1$-$C_3$)-alkyl,
—($C_1$-$C_2$)-alkylene-S(O)$_2$-phenyl, —($C_1$-$C_3$)-alkylene-O—R10 or —($C_0$-$C_4$)-alkylene-heterocyclyl, wherein heterocyclyl is as defined below and is unsubstituted or mono- or disubstituted independently of one another by R8, R6 is heterocyclyl, wherein heterocyclyl is selected out of the group benzisoxazolyl, isoxazolyl, morpholinyl, pyridyl, thiazolyl, thiadiazolyl or thienyl, and wherein heterocyclyl is independently of one another unsubstituted or mono-, di- or trisubstituted by R7, R7 is chlorine or =O,
R8 is —($C_3$-$C_6$)-cycloalkyl, —$NH_2$, —($C_1$-$C_4$)-alkyl, or heterocyclyl, wherein heterocyclyl is as defined above and wherein heterocyclyl is independently of one another unsubstituted or mono- or disubstituted by R7, R10 is hydrogen atom, —($C_0$-$C_2$)-alkylene-($C_3$-$C_6$)-cycloalkyl or —($C_1$-$C_4$)-alkyl, R21 and R22 are independently of one another identical or different and are hydrogen atom or
—($C_1$-$C_4$)-alkyl, R21 and R22 together with the nitrogen atom to which they are bonded can form a heterocyclic ring from the group N-methyl-piperazine or morpholine, $G_1$ is —($C_2$-$C_4$)-alkylene, wherein —($C_2$-$C_4$)-alkylene is unsubstituted or mono- or disubstituted independently of one another by R13, R13 is a hydrogen atom, —($C_1$-$C_2$)-alkylene-O—R22, —($C_1$-$C_2$)-alkylene-OH, —($C_0$-$C_2$)-alkylene-C(O)—OH, —(C₀-C₁)-alkylene-C(O)—N(R21)-R22, or —(C₁-C₄)-alkyl, or R13 and R3 together with the atoms to which they are bonded form a isothiazolidine 1,1-dioxide, [1,2]thiazinane 1,1-dioxide or [1,4,3]oxathiazinane 4,4-dioxide group and wherein said group is unsubstituted or substituted one time by =O, G₂ is azetidine, piperazine or piperidine, wherein G2 is unsubstituted or monosubstituted by isopropyl, cyclopropyl, benzyl or pyridyl, in all its stereoisomeric forms and mixtures thereof in any ratio, and its physiologically tolerable salts.

6) The present invention also relates to the compounds of the formula I, which are 5-Chloro-thiophene-2-carboxylic acid [2-(1-isopropyl-piperidin-4-ylsulfamoyl)-ethyl]-amide, 5-Chloro-thiophene-2-carboxylic acid [2-(1-cyclopropyl-piperidin-4-ylsulfamoyl)-ethyl]-amide, 5-Chloro-thiophene-2-carboxylic acid {2-[(1-isopropyl-piperidin-4-yl)-methyl-sulfamoyl]-ethyl}-amide, 5-Chloro-thiophene-2-carboxylic acid {2-[(1-isopropyl-piperidin-4-yl)-(2,2,2-trifluoro-ethyl)-sulfamoyl]-ethyl}-amide, 5-Chloro-thiophene-2-carboxylic acid [2-(3,4,5,6-tetrahydro-2H-[1,4']bipyridinyl-4-ylsulfamoyl)-ethyl]-amide, 5-Chloro-thiophene-2-carboxylic acid[2-(azetidin-3-ylsulfamoyl)-ethyl]-amide, 5-Chloro-thiophene-2-carboxylic acid [2-(1-isopropyl-azetidin-3-ylsulfamoyl)-ethyl]-amide, 5-Chloro-thiophene-2-carboxylic acid [2-(4-benzyl-piperazin-1-ylsulfamoyl)-ethyl]-amide, 5-Bromo-thiophene-2-carboxylic acid [2-(1-isopropyl-piperidin-4-ylsulfamoyl)-ethyl]-amide, 5-Methyl-thiophene-2-carboxylic acid [2-(1-isopropyl-piperidin-4-ylsulfamoyl)-ethyl]-amide, 5-Bromo-furan-2-carboxylic acid [2-(1-isopropyl-piperidin-4-ylsulfamoyl)-ethyl]-amide, 4-Chloro-N-[2-(1-isopropyl-piperidin-4-ylsulfamoyl)-ethyl]-benzamide, 5-Chloro-pyridine-2-carboxylic acid[2-(1-isopropyl-piperidin-4-ylsulfamoyl)-ethyl]-amide, 3-Chloro-N-[2-(1-isopropyl-piperidin-4-ylsulfamoyl)-ethyl]-benzamide, 5-Chloro-thiophene-2-carboxylic acid {2-[(1-isopropyl-piperidin-4-yl)-(2-methoxy-ethyl)-sulfamoyl]-ethyl}-amide, 5-Chloro-thiophene-2-carboxylic acid {2-[(2-hydroxy-ethyl)-(1-isopropyl-piperidin-4-yl)-sulfamoyl]-ethyl}-amide, 5-Chloro-thiophene-2-carboxylic acid {2-[(3-hydroxy-propyl)-(1-isopropyl-piperidin-4-yl)-sulfamoyl]-ethyl}-amide, 5-Chloro-thiophene-2-carboxylic acid {2-[dimethylcarbamoylmethyl-(1-isopropyl-piperidin-4-yl)-sulfamoyl]-ethyl}-amide, 5-Chloro-thiophene-2-carboxylic acid {2-[(1-isopropyl-piperidin-4-yl)-(2-morpholin-4-yl-2-oxo-ethyl)-sulfamoyl]-ethyl}-amide, 5-Chloro-thiophene-2-carboxylic acid {2-[carbamoylmethyl-(1-isopropyl-piperidin-4-yl)-sulfamoyl]-ethyl}-amide, 5-Chloro-thiophene-2-carboxylic acid {2-[(1-isopropyl-piperidin-4-yl)-(5-methyl-isoxazol-3-ylmethyl)-sulfamoyl]-ethyl}-amide, 5-Chloro-thiophene-2-carboxylic acid {2-[(1-isopropyl-piperidin-4-yl)-pyridin-3-ylmethyl-sulfamoyl]-ethyl}-amide, 5-Chloro-thiophene-2-carboxylic acid {2-[(1-isopropyl-piperidin-4-yl)-thiazol-2-ylmethyl-sulfamoyl]-ethyl}-amide, 5-Chloro-thiophene-2-carboxylic acid {2-[(1-isopropyl-piperidin-4-yl)-propylaminocarbonyl-sulfamoyl]-ethyl}-amide, 5-Chloro-thiophene-2-carboxylic acid {2-[acetyl-(1-isopropyl-piperidin-4-yl)-sulfamoyl]-ethyl}-amide, 5-Chloro-thiophene-2-carboxylic acid [2-(1-isopropyl-piperidin-4-ylsulfamoyl)-propyl]-amide, 5-Chloro-thiophene-2-carboxylic acid [(S)-1-hydroxymethyl-2-(1-isopropyl-piperidin-4-ylsulfamoyl)-ethyl]-amide, 5-Chloro-thiophene-2-carboxylic acid [2-(1-isopropyl-piperidin-4-ylsulfamoyl)-1,1-dimethyl-ethyl]-amide, 5-Chloro-thiophene-2-carboxylic acid [3-(1-isopropyl-piperidin-4-ylsulfamoyl)-propyl]-amide, 4-[(5-Chloro-thiophene-2-carbonyl)-amino]-3-(1-isopropyl-piperidin-4-ylsulfamoyl)-butyric acid, 5-Chloro-thiophene-2-carboxylic acid [2-(1-isopropyl-piperidin-4-yl)-1,1,3-trioxo-1$\lambda^6$-isothiazolidin-5-ylmethyl]-amide, 5-Chloro-thiophene-2-carboxylic acid {2-[[5-(5-chloro-thiophen-2-yl)-isoxazol-3-ylmethyl]-(1-isopropyl-piperidin-4-yl)-sulfamoyl]-ethyl}-amide, 5-Chloro-thiophene-2-carboxylic acid {2-[(5-cyclopropyl-[1,3,4]thiadiazol-2-ylmethyl)-(1-isopropyl-piperidin-4-yl)-sulfamoyl]-ethyl}-amide or 5-Chloro-thiophene-2-carboxylic acid {2-[[(5-chloro-pyridin-2-ylcarbamoyl)-methyl]-(1-isopropyl-piperidin-4-yl)-sulfamoyl]-ethyl}-amide.

As used herein, the term alkyl is to be understood in the broadest sense to mean hydrocarbon residues which can be linear, i.e. straight-chain or branched. Further, the term alkyl as used herein expressly includes saturated groups as well as unsaturated groups which latter groups contain one or more, for example one, two or three, double bonds and/or triple bonds. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—$(C_0-C_6)$-alkyl" or "—$(C_0-C_8)$-alkylene" is an alkyl residue containing 1, 2, 3, 4, 5, 6, 7 or 8 carbon atoms. The term "—$C_0$-alkyl" or "—$C_0$-alkylene" is a covalent bond. Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of —$(C_3-C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The term "a monocyclic or bicyclic 6- to 14-membered aryl" or "—$(C_6-C_{14})$-aryl" are understood as meaning aromatic hydrocarbon radicals containing from 6 to 14 carbon atoms in the ring. Examples of —$(C_6-C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals. The term "-heterocyclyl" refers to a heterocycle in which one or more of the 4 to 15 ring carbon atoms are replaced by heteroatoms such as nitrogen, oxygen or sulfur.

Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2, 4-triazolyl, 1,2,5-triazolyl, 1,3,4-triazolyl and xanthenyl.

The term "R9 and R11 together with the carbon atom to which they are bonded can form a 3- to 6 membered carbocyclic ring" refer to structures, which can be derived from compounds such as cyclopropyl, cyclobutyl, cyclopentyl or cyclohexyl.

The term "R13 and R3 together with the atoms to which they are bonded form a 5- to 7-membered cyclic group, wherein one of the carbon atoms within said cyclic group can be replaced by nitrogen, oxygen or sulphur" refer to structures, which can be derived from compounds such as isothiazolidine 1,1-dioxide; 2,5-dihydro-isothiazole 1,1-dioxide; 2,3-dihydro-isothiazole 1,1-dioxide; [1,2]thiazinane 1,1-dioxide; 2H-[1,2]thiazine 1,1-dioxide; 5,6-dihydro-2H-[1,2]thiazine 1,1-dioxide; 3,4-dihydro-2H-[1,2]thiazine 1,1-dioxide; 3,6-dihydro-2H-[1,2]thiazine 1,1-dioxide; [1,2]thiazepane 1,1-dioxide; 2,5,6,7-tetrahydro-[1,2]thiazepine 1,1-dioxide; 2,7-dihydro-[1,2]thiazepine 1,1-dioxide; 2,5-dihydro-[1,2]thiazepine 1,1-dioxide; [1,2,4]thiadiazolidine 1,1-dioxide; [1,2,3]thiadiazolidine 1,1-dioxide; 2,5-dihydro-[1,2,4]thiadiazole 1,1-dioxide; [1,3,4]oxathiazolidine 3,3-dioxide; [1,3,2]oxathiazo-lidine 3,3-dioxide; [1,4,2]dithiazolidine 1,1-dioxide; [1,3,2]dithiazolidine 1,1-dioxide; [1,2,5]thiadiazinane 1,1-dioxide; [1,3,4]oxathiazinane 3,3-dioxide; [1,4,3]oxathiazinane 4,4-dioxide; [1,5,2]dithiazinane 1,1-dioxide; [1,2,6]thiadiazepane 1,1-dioxide; [1,3,4]oxathiazepane 3,3-dioxide or [1,6,2]dithiazepane 1,1-dioxide.

The term "R21 and R22 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refers to structures, which can be derived from compounds such as azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketomorpholine, ketopiperazine, ketothiomorpholine, morpholine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole.

The term "oxo-residue" or "=O" refers to residues such as carbonyl (—C(O)—), sulfinyl (—S(O)—) or nitroso (—N=O).

Ring systems wherein "X is sulfur, nitrogen, oxygen or the residues —CH=CH— or —CH=N—" refer to residues such as furanyl, phenyl, pyridyl, pyrrolyl or thiophenyl.

The term "if two R13 are attached to the same carbon atom they can form together a 3- to 8-membered carbocyclic ring" refers to cycloalkyl residues with 3 to 8 carbon atoms in the ring. This ring structures are integrated into the compounds of the formula I e.g. as shown for the following cyclopropyl residue:

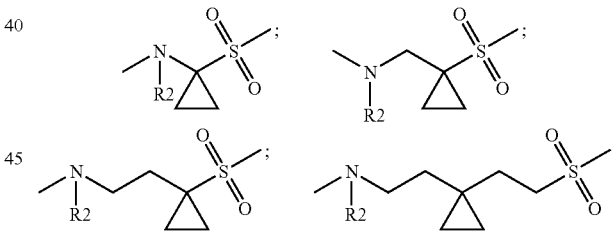

The term "—$(C_1$-$C_3)$-perfluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$,
—$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$,
—$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$,
—$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$,
—$CF_2$—$CF_2$—$CHF_2$ or —$CF_2$—$CF_2$—$CH_2F$.

The term "—$(C_1-C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—,
—$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—,
—$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—$CF_2$—$CH_2$—$CF_2$—,
—$CF_2$—$CH_2$—$CHF$—, —$CF_2$—$CF_2$—$CF_2$—, or —$CF_2$—$CF_2$—$CHF$—.

Halogen is fluorine, chlorine, bromine or iodine, preferably fluorine, chlorine or bromine, particularly preferably chlorine or bromine.

Optically active carbon atoms present in the compounds of the formulae I or Ia can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I or Ia and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I or Ia.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I or Ia can also be obtained by employing stereochemically uniform starting materials or by using stereoselective reactions.

Physiologically tolerable salts of the compounds of formulae I or Ia are nontoxic salts that are physiologically acceptable, in particular pharmaceutically utilizable salts. Such salts of compounds of the formula I or Ia containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I or Ia, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formulae I or Ia, which simultaneously contain a basic group and an acidic group, for example a guanidino group and a carboxyl group, can also be present as zwitterions (betaines), which are likewise included in the present invention.

Salts of compounds of the formulae I or Ia can be obtained by customary methods known to those skilled in the art, for example by combining a compound of the formulae I or Ia with an inorganic or organic acid or base in a solvent or dispersant, or from other salts by cation exchange or anion exchange. The present invention also includes all salts of the compounds of the formulae I or Ia which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts. The present invention furthermore includes all solvates of compounds of the formulae I or Ia for example hydrates or adducts with alcohols.

The invention also includes derivatives and modifications of the compounds of the formula I, for example prodrugs, protected forms and other physiologically tolerable derivatives, as well as active metabolites of the compounds of the formulae I or Ia. The invention relates in particular to prodrugs and protected forms of the compounds of the formulae I or Ia, which can be converted into compounds of the formula I under physiological conditions. Suitable prodrugs for the compounds of the formulae I or Ia, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formulae I or Ia are especially acyl prodrugs and carbamate prodrugs of acrylatable nitrogen-containing groups such as amino groups and the guanidino group and also ester prodrugs and amide prodrugs of carboxylic acid groups which may be present in compounds of the formulae I or Ia. In the acyl prodrugs and carbamate prodrugs one or more, for example one or two, hydrogen atoms on nitrogen atoms in such groups are replaced with an acyl group or a carbamate, preferably a —$(C_1-C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, Heterocyclyl-, $(C_6-C_{14})$-aryl-$(C_1-C_4)$-alkyl- or Heterocyclyl-$(C_1-C_4)$-alkyl- and in which $R^{p2}$ has the meanings indicated for $R^{p1}$ with the exception of hydrogen.

The compounds of the formulae I or Ia can be prepared by utilising procedures and techniques, which per se are well known and appreciated by one of ordinary skill in the art. Starting materials or building blocks for use in the general synthetic procedures that can be applied in the preparation of the compounds of formulae I or Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formulae I or Ia can be prepared, for example in the course of a convergent synthesis, by linking two or more fragments which can be derived retrosynthetically from the formula I. More specifically, suitably substituted starting aminoalkylsulfonyl derivatives are employed as building blocks in the preparation of the compounds of formula I. If not commercially available, such aminoalkylsulfonyl derivatives can be prepared according to the well-known standard procedures for the formation of the aminoalkylsulfonyl system. By choosing suitable precursor molecules, these aminoalkylsulfonamide syntheses allow the introduction of a variety of substituents into the various positions of the aminoalkylsulfonamide system, which can be chemically modified in order to finally arrive at the molecule of the formula I having the desired substituent pattern.

In the following, procedures of particular interest for the embodiment of this invention are listed and referenced briefly, however, they are standard procedures comprehensively discussed in the literature, and are well known to one skilled in the art. Although not always shown explicitly, in certain cases isomers will occur during the synthesis of the below mentioned reactions. Nevertheless such mixtures of isomers can be separated by modern separation techniques like, for example, preparative HPLC.

1) Typically, aminoalkylsulfonamides are prepared by the reaction of N-protected aminoalkyl-sulfonyl chlorides with various amines in the presence of a base.

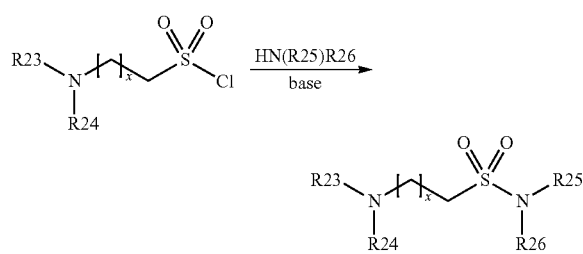

If R23 and R24 are protecting groups, these groups can be subsequently removed and the resulting amine can be coupled with a thiophene-2-carboxylic acid under standard peptide coupling conditions. For example, a phthaloyl protected β-aminoethylsulfonylchloride, which is commercially available, can be transformed to the corresponding sulfonamides. Subsequent removal of the phthaloyl-protecting group leads to N-unprotected β-aminoethylsulfonamides, which can be further modified by standard procedures, for example acylated by a 2-thiophene-carboxylic acid in the presence of a typical coupling reagent to give compounds of the formula Ia, which are of particular interest of this application.

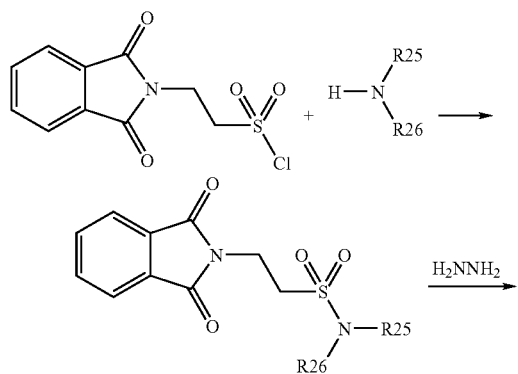

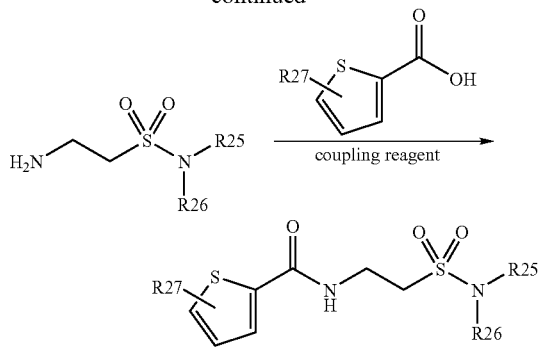

2) Specifically substituted β-aminoethylsulfonyl derivatives, which are of particular interest of this application, can be synthesized by a Michael-type addition of appropriate amines to optionally substituted ethenesulfonic acid amides. (See for example Vessiere, R. et al. Synthesis (1983) 816; Tsuge, H. et al. Heterocyclic Communications (1997) 3, 19.)

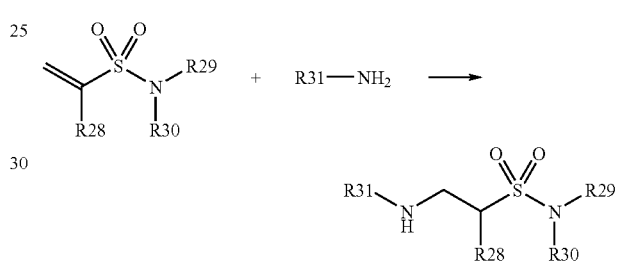

3) In order to obtain substituted secondary sulfonamides, primary sulfonamides can be selectively substituted at the nitrogen atom by the reaction with typical electrophiles R33-X (, in which X is a leaving group, such as chloride, bromide, iodide, mesylate or tosylate) in the presence of a base, for example $K_2CO_3$. (See for example Liskamp, R. M. et al. J. Org. Chem. (2000) 69, 11, 3662). Pg has the meaning of a protecting group.

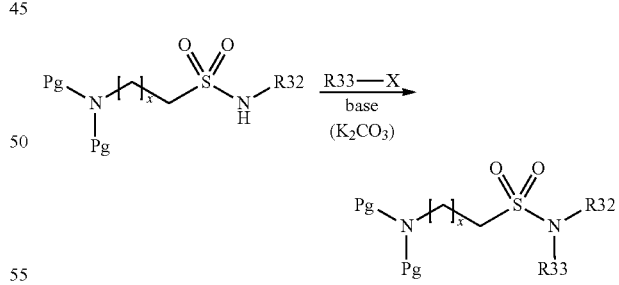

4) α-substituted β-aminoethylsulfonamides can be prepared, for example, by deprotonation of N-protected (for example phthaloyl protected) β-aminoethylsulfonamides with a base such as LDA or NaH and subsequent reaction with electrophiles. (For representative examples see: Liskamp, R. et al. Tetrahedron (1993) 49, 1133.) When reacting the deprotonated β-aminoethylsulfonamide with an aldehyde, β-aminoethylsulfonamides with a hydroxy-methylene side-chain can be obtained, which can be further modified by standard procedures.

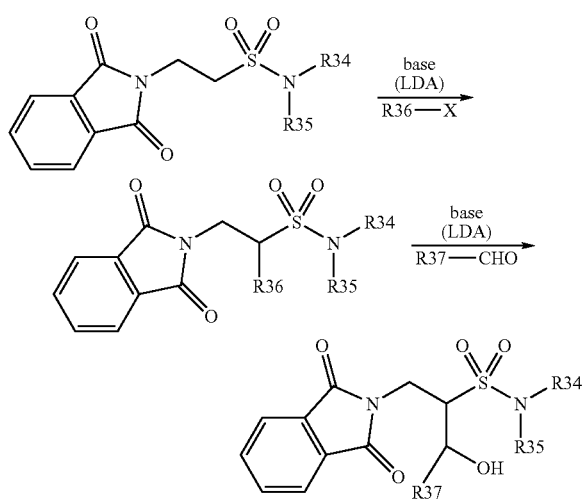

5) β-substituted β-aminoethylsulfonamides can be obtained starting from the commercially available N-protected α-amino acids. Treatment of an N-protected α-amino acid with a condensing agent (for example isobutyl chloroformate) in the presence of a suitable base, followed by reaction of the resulting anhydride intermediate with a suitable reducing agent (for example $NaBH_4$) gives a 2-N-protected aminoethanol intermediate. The 2-N-protected aminoethanol intermediate can be reacted with an alkylsulfonyl halide (for example methanesulfonylchloride) in the presence of a base to provide the corresponding alkylsulfonyloxy derivative. Subsequent reaction with cesium thiolacetate leads to a thioester which upon treatment with chlorine gas provides a N-protected β-substituted β-aminoethylsulfonylchloride. (See: Palmer, J. et al. WO 03/024923 or Liskamp, R. M. et al. Synthesis (2000) 1579). Reaction with appropriate amines provide the N-protected-β-substituted β-aminoethylsulfonamides, which can be further modified to structures of the formula I.

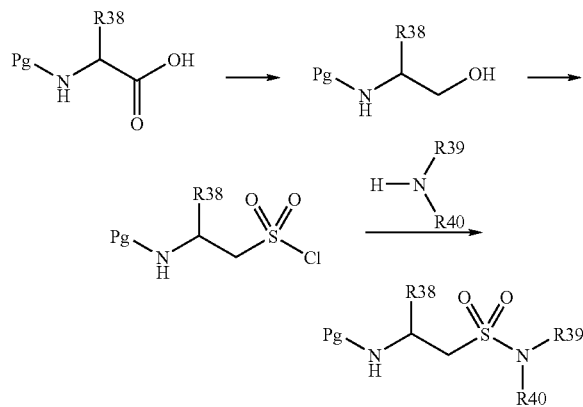

Further, in order to obtain the desired substituents at the aminoalkylsulfonamide system in the formula I, the functional groups introduced during the aminoalkylsulfonamide synthesis can be chemically modified. Especially the groups present in the aminoalkylsulfonamide system can be modified by a variety of reactions and thus the desired residues R13 in $G_1$ of formula I can be obtained. Hydroxymethyl groups as well as formyl groups attached to the aminoalkylsulfonamide system can be transformed to a variety of functional groups, for example to the corresponding carboxylic acid or carboxylic ester by many oxidative reactions well known to those skilled in the art. Moreover a nitrile group attached to the aminoalkylsulfonamide can, for example, easily be converted into the desired acid under acidic, basic or reductive conditions. In addition, carboxylic acid groups and acetic acid groups can be converted into their homologues by usual reactions for chain elongation of carboxylic acids. Halogen atoms can be introduced into aromatic side chains, for example according to procedures like the following described in the literature. For the fluorination N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203) however, other suitable fluorinating reagents may also be employed where appropriate. The chlorination, bromination, or iodination of aromatic side chains can be accomplished by the reaction with elemental halogens or by the use of NCS, NBS or NIS and many other reagents well known to those skilled in the art. Depending on the reaction conditions, reagent, stochiometry and substitution pattern the halogen is introduced in the different positions of an aromatic side chain of the β-aminoalkylsulfonamide. By selective halogen/metal exchange or metalation by selective hydrogen/metal exchange and subsequent reaction with a wide range of electrophiles various substituents can be introduced at the aromatic nucleus. (M. R. Grimmett, Heterocycles (1994) 37, 2087; V. D. Gardner et al., J. Heterocycl. Chem. (1984) 21, 121; D. Butler et al., J. Org. Chem. (1971) 36, 2542). Halogens or hydroxy groups (via their triflates or nonaflates)—or primary amines (via their diazonium salts) present in the side chain of the aminoalkylsulfonamide—can be converted directly, or after interconversion to the corresponding stannane, or boronic acid, into a variety of other functional groups like for example —CN, —$CF_3$, —$C_2F_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. (1998) 110, 2154; B. Yang, S. Buchwald, J. Organomet. Chem. (1999) 576, 125; T. Sakamoto, K. Ohsawa, J. Chem. Soc. Perkin Trans I (1999) 2323; D. Nichols, S. Frescas, D. Marona-Lewicka, X. Huang, B. Roth, G. Gudelsky, J. Nash, J. Med. Chem. (1994) 37, 4347; P. Lam, C. Clark, S. Saubern, J. Adams, M. Winters, D. Chan, A. Combs, Tetrahedron Lett. (1998) 39, 2941; D. Chan, K. Monaco, R. Wang, M. Winters, Tetrahedron Lett. (1998) 39, 2933; V. Farina, V. Krishnamurthy, W. Scott, The Stille Reaction, Wiley, 1994; F. Qing et al. J. Chem. Soc. Perkin Trans. I (1997) 3053; S. Buchwald et al. J. Am. Chem. Soc. (2001) 123, 7727; S. Kang et al. Synlett (2002) 3, 427; S. Buchwald et al. Organic Lett. (2002) 4, 581; T. Fuchikami et al. Tetrahedron Lett. (1991) 32, 91; Q. Chen et al. Tetrahedron Lett. (1991) 32, 7689).

For example, nitro groups can be reduced to amino groups by means of various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce the residues R13 in $G_1$ of the formula I, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the aminoalkylsulfonamide can be hydrolyzed to the corresponding carboxylic acids, which after activation can then be reacted with amines or alcohols under standard conditions to give amides or esters, respectively. Ester groups present in the aminoalkyl-sulfonamide can be converted to other esters by transesterification. Carboxylic acids attached to a suitable aminoalkylsulfonamide can also be alkylated to give esters. Ether groups present at the aminoalkylsulfonamide derivative, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a aminoalkylsulfonyl derivative it may in certain cases become necessary to specifically adapt reaction conditions or to choose specific reagents from a variety of reagents that can in principle be employed in a conversion reaction, or otherwise to take specific measures for achieving a desired conversion, for example to use protecting group techniques. However, finding out suitable reaction variants and reaction conditions in such cases does not cause any problems for one skilled in the art.

The structural elements present in the residues attached to the aminoalkylsulfonamide in the compounds of the formula I can be introduced into the aminoalkylsulfonyl derivative obtainable as outlined above by consecutive reaction steps using synthesis methodologies like those outlined below using procedures which per se are well known to one skilled in the art.

The invention also refers to a process for the preparation of a compound of formula I, which comprises condensing a compound of formula 2 with a compound of formula $HN(R^{43})R^{44}$ to give a compound of the formula 3 and optionally converting the compound of the formula 3 into a compound of the formulae I or Ia,

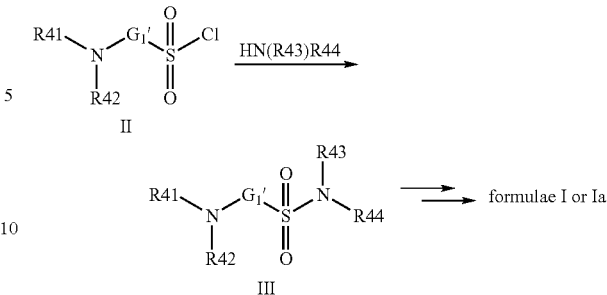

wherein the residue $HN(R^{43})R^{44}$ has the donation of $—N(R^3)G_2$ as defined in the formula I, wherein $—N(R^{41})R^{42}$ has either the donation of $—N(R^2)C(O)$-heterocycle, wherein heterocycle is a residue out of the group selected from furanyl, phenyl, pyridyl, pyrrolyl or thiophenyl, and is substituted by $R^1$ and V, and wherein $R^2$ is defined as in formula I, or optionally the residue $—N(R^{41})R^{42}$ has the meaning of a precursor group, which can be subsequently converted into the residues $—N(R^2)C(O)$-heterocycle of the formulae I or Ia. If $—N(R^{41})R^{42}$ is a precursor group of $—N(R^2)C(O)$-heterocycle, $R^{41}$ or $R^{42}$ can have the meaning of a protecting group suitable for nitrogen atom protection (see, for example, Greene and Wuts, Protective Groups in Organic Synthesis, Wiley, 1991, or P. Kocienski, Protecting Groups, Thieme 1994), for example the residue $—N(R^{41})R^{42}$ can have the meaning of

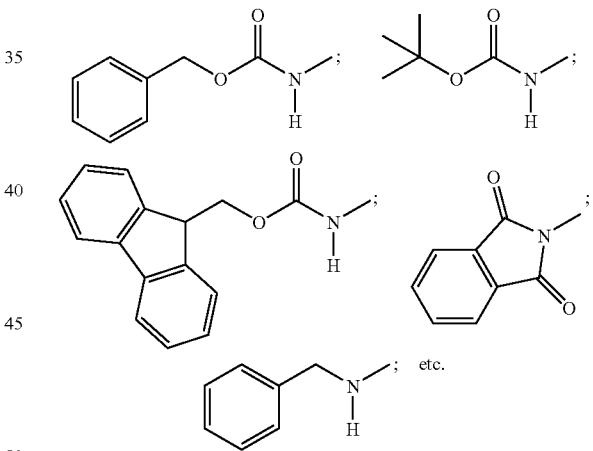

Thus, the residue $—N(R^{43})R^{44}$ can have the denotations of $—N(R^3)G_2$, respectively, given above or in addition in the residues $R^{43}$ and $R^{44}$ functional groups can also be present in the form of groups that can subsequently be transformed into the final groups $R^3$ and $G_2$, i.e. functional groups can be present in the form of precursor groups or of derivatives, for example in protected form. In the course of the preparation of the compounds of the formulae I or Ia, it can generally be advantageous or necessary to introduce functional groups which reduce or prevent undesired reactions or side reactions in the respective synthesis step, in the form of precursor groups which are later converted into the desired functional groups, or to temporarily block functional groups by a protecting group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups cyano groups and nitro groups may be mentioned. The cyano group can in a later step be transformed into carboxylic acid derivatives or by reduction into aminomethyl groups, or nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000).

The residue —N($R^{41}$)$R^{42}$ in the compounds of the formulae 2 and 3 can denote the group —N($R^2$)C(O)-heterocycle as defined above which finally is to be present in the desired target molecule of the formula I, or it can denote a group which can subsequently be transformed into the group —N($R^2$)C(O) heterocycle, for example a precursor group or a derivative of the group —N($R^2$)C(O) heterocycle in which functional groups are present in protected form, or $R^{41}$ and $R^{42}$ can independently from each other denote a hydrogen atom or a protective group for the nitrogen atom of the aminalkylsulfonyl derivative. Similarly, the residues $R^{13'}$, which are attached to the alkyl chain in $G_1'$ in formulae 2 and 3, have the corresponding definitions of $R^{13}$ in formula I as defined above, however, for the synthesis of the compounds of the formula I these residues, too, can in principle be present at the stage of the condensation of a compound of the formula 2 with a compound of the formula HN($R^{43}$)$R^{44}$ giving a compound of the formula 3 in the form of precursor groups or in protected form.

The compounds of the formula 2 can usually be prepared by standard procedures from the corresponding sulfonic acids by treatment with phosgene, thionylchloride or phosphorus pentachloride (in the presence of catalytic DMF) or other standard reagents for the chlorination of sulfonic acids.

If the residue —C(O)— heterocycle-$R^1$ and $R^2$ present in an aminoalkylsulfonamide of the formula I or the residues $R^{41}$ and $R^{42}$ present in an aminoalkylsulfonyl derivative of the formula 2, or a residue in which functional groups within the residues —C(O)-heterocycle-$R^1$, $R^2$, $R^{41}$ or $R^{42}$ are present in protected form or in the form of a precursor group, have not already been introduced during a preceding step, for example during a synthesis of the aminoalkylsulfonamide, these residues can, for example, be introduced into the aminoalkylsulfonamide system by conventional literature procedures for N-alkylation, reductive amination, N-arylation, N-acylation or N-sulfonylation of the nitrogen atoms of the aminoalkylsulfonyl derivative well known to one skilled in the art. N-Acylation of a nitrogen atom, for example with substituted thiophene carboxylic acid derivatives to produce finally compounds of the formulae I or Ia, can, for example, be performed under standard conditions by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene) amino)-N,N,N',N'-tetramethyluronium tetrafluoroborate (TOTU), O-(7-aza-benzotriazole-1-yl)-N,N,N',N'-tetramethyluronium-hexafluorophosphate (HATU), diethylphosphoryl cyanide (DEPC) or bis-(2-oxo-3-oxazolidinyl)-phosphoryl chloride (BOP-Cl) and many others. N-Acylation can also be performed by the reaction with a corresponding acid-chloride, -fluoride or -bromide or a corresponding anhydride.

As stated above the residues $R^{13}$ in $G_1$ can be present at the stage of the aminoalkylsulfonyl derivative of the formula 2, for example, by de novo synthesis of the aminoalkylsulfonyl system as indicated above. Otherwise, the residues $R^{13'}$ can be introduced in the sulfonamide derivatives of the formula 3 by deprotonation with strong bases such as LDA or NaH and subsequent reaction with electrophiles. These residues $R^{13'}$, which are attached to $G_1'$ in formula 3, have the corresponding definitions of $R^{13}$ in formula I as defined above, or they can have the meaning of precursor groups, which can finally be transformed to the residues $R^{13}$ of the formula I.

Preferred methods include, but are not limited to those described in the examples.

The compounds of the present invention are serine protease inhibitors, which inhibit the activity of the blood coagulation enzyme factor Xa. They are specific serine protease inhibitors inasmuch as they do not substantially inhibit the activity of other proteases whose inhibition is not desired. The activity of the compounds of the formulae I or Ia can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa the compounds of the formulae I or Ia and their physiologically tolerable salts and their prodrugs are generally suitable for the therapy and prophylaxis of conditions in which the activity of factor Xa plays a role or has an undesired extent, or which can favorably be influenced by inhibiting factor Xa or decreasing their activities, or for the prevention, alleviation or cure of which an inhibition of factor Xa or a decrease in their activity is desired by the physician. As inhibition of factor Xa influences blood coagulation and fibrinolysis, the compounds of the formulae I or Ia and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound of the formula I or a physiologically tolerable salt or a prodrug thereof, as well as pharmaceutical preparations therefore.

The present invention also relates to the use of the compounds of the formulae I or Ia and/or their physiologically tolerable salts and/or their prodrugs for the production of pharmaceuticals for inhibition of factor Xa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formulae I or Ia and/or their physiologically tolerable salts and/or their prodrugs for the inhibition of factor Xa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formulae I or Ia and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formulae I or Ia can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formulae I or Ia and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I or Ia and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I or Ia and/or their physiologically tolerable salts and/or their prodrugs. The amount of the active ingredient of the formulae I or Ia and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I or Ia and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I or Ia, and/or their physiologically tolerable salts and/or their prodrugs. In case a pharmaceutical preparation contains two or more compounds of the formulae I or Ia, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I or Ia allows a great deal of control over the biological and physico-chemical properties of the compounds and thus allows the selection of such desired compounds. Furthermore, in addition to at least one compound of the formulae I or Ia and/or a physiologically tolerable salt and/or its prodrug, the pharmaceutical preparations can also contain one or more other therapeutically or prophylactically active ingredients.

When using the compounds of the formulae I or Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I or Ia can also advantageously be used as an anticoagulant outside an individual. For example, an effective amount of a compound of the invention can be contacted with a freshly drawn blood sample to prevent coagulation of the blood sample. Further, a compound of the formulae I or Ia or its salts can be used for diagnostic purposes, for example in in vitro diagnoses, and as an auxiliary in biochemical investigations. For example, a compound of the formulae I or Ia can be used in an assay to identify the presence of factor Xa or to isolate factor Xa in a substantially purified form. A compound of the invention can be labeled with, for example, a radioisotope, and the labeled compound bound to factor Xa is then detected using a routine method useful for detecting the particular label. Thus, a compound of the formulae I or Ia or a salt thereof can be used as a probe to detect the location or amount of factor Xa activity in vivo, in vitro or ex vivo.

Furthermore, the compounds of the formulae I or Ia can be used as synthesis intermediates for the preparation of other compounds, in particular of other pharmaceutical active ingredients, which are obtainable from the compounds of the formulae I or Ia, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid, formic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Abbreviations used:
tert-Butyl tBu
2,2'-bis(diphenylphoshino-1,1'-binaphthyl Binap
Bis-(oxo-3-oxazolidinyl)-phosphoryl chloride BOP-Cl
dibenzylidenacetone dba
Dichloromethane DCM
Dicyclohexyl-carbodiimide DCC
Diethylphosphoryl cyanide DEPC
Diisopropylethylamine DIPEA
4-Dimethyaminopyridine DMAP
N,N-Dimethylformamide DMF
Dimethylsulfoxide DMSO
1,1'-Bis(diphenylphosphino)ferrocene DPPF
O-(7-Azabenzotriazol-1-yl)-N,N,N',N'-tetramethyluronium-hexafluorophosphate HATU
Lithium diisopropylamide LDA
N-Bromosuccinimide NBS
N-Chlorosuccinimide NCS
N-Iodosuccinimide NIS
N-Ethylmorpholine NEM
Methanol MeOH
Room temperature 20° C. to 25° C. RT
Saturated sat.
Tetrahydrofuran THF
Trifluoroacetic acid TFA
O-((Ethoxycarbonyl)cyanomethyleneamino)-N,N,N',N'-tetramethyluronium tetrafluoroborate TOTU Example 1

5-Chloro-thiophene-2-carboxylic acid [2-(1-isopropyl-piperidin-4-ylsulfamoyl)-ethyl]-amide i) 2-(1,3-Dioxo-1,3-dihydro-isoindol-2-yl)-ethanesulfonic acid (1-isopropyl-piperidin-4-yl)-amide 1.00 g (7.032 mmol) 1-Isopropyl-piperidin-4-ylamine (commercially available, or obtainable as described in EP 1479676) was dissolved in 100 ml dichloromethane. Subsequently 1.38 ml (1.1 equiv.) diisopropylethylamine (DIPEA) and 2.12 g (1.1 equiv.) 2-(1,3-dioxo-1,3-dihydro-isoindol-2-yl)-ethanesulfonyl chloride (commercially available) were added. The resulting mixture was stirred for 5 h at room temperature. After complete conversion the mixture was diluted with 100 ml dichloromethane and washed with 150 ml water. The organic phase was then washed with 100 ml of a half saturated $NaHCO_3$-solution and finally with brine. Drying over anhydrous $MgSO_4$ and removal of the solvent by evaporation under reduced pressure gave crude 2-(1,3-dioxo-1,3-dihydro-isoindol-2-yl)-ethanesulfonic acid (1-isopropyl-piperidin-4-yl)-amide as a light yellow foam. Yield: 2.48 g MS ($ES^+$): m/e=380.

ii) 2-Amino-ethanesulfonic acid (1-isopropyl-piperidin-4-yl)-amide 2.48 g (6.53 mmol) crude 2-(1,3-dioxo-1,3-dihydro-isoindol-2-yl)-ethanesulfonic acid (1-isopropyl-piperidin-4-yl)-amide were dissolved in 100 ml ethanol. 65.3 ml (10 equiv.) of a 1M hydrazine-solution in THF and 124 mg (0.1 equiv.) p-toluenesulfonic acid were added. The resulting mixture was stirred at 60° C. for 72 h. The formed precipitate was filtered off. The filtrate was concentrated under reduced pressure. The resulting residue was co-distilled three times with 200 ml DMF to remove the excess hydrazine. Crude 2-amino-ethanesulfonic acid (1-isopropyl-piperidin-4-yl)-amide was obtained as a colorless oil. Yield: 2.00 g
MS ($ES^+$): m/e=250.

iii) 5-Chloro-thiophene-2-carboxylic acid [2-(1-isopropyl-piperidin-4-ylsulfamoyl)-ethyl]-amide To a solution of 1.87 g (1.75 equiv.) 5-chloro-thiophene-2-carboxylic acid in 50 ml DMF were added 4.39 g (1.75 equiv.) HATU and 3.35 ml (3 equiv.) DIPEA. The resulting mixture was stirred for 30 min at room temperature. Subsequently a solution of 1.64 g (6.58 mmol) 2-amino-ethanesulfonic acid (1-isopropyl-piperidin-4-yl)-amide and 1.11 ml (1 equiv.) DIPEA in 20 ml DMF was added. The resulting mixture was stirred at room temperature overnight and concentrated under reduced pressure. The resulting residue was taken up in ethyl acetate and filtered. The filtrate was washed with a saturated $NaHCO_3$-solution. Then, the product was extracted into the aqueous phase by treatment with a 0.1 N HCl-solution. Separation of the aqueous phase, then adjusting the pH to ≈9 by treatment with a saturated $NaHCO_3$-solution and subsequent re-extraction with ethyl acetate brought the product back in the organic phase. Concentration under reduced pressure afforded crude 5-chloro-thiophene- 2-carboxylic acid [2-(1-isopropyl-piperidin-4-ylsulfamoyl)-ethyl]-amide. Final purification was achieved by preparative RP-HPLC (CH$_3$CN/H$_2$O gradient+0.1% TFA). Lyophilisation and transformation into its hydrochloride gave the title compound as a colorless, amorphous solid. Yield: 1.76 g MS (ES$^+$): m/e=394, chloro pattern.

5-Chloro-thiophene-2-carboxylic acid [2-(1-isopropyl-piperidin-4-ylsulfamoyl)-ethyl]-amide can also be prepared by reacting 5-chloro-thiophene-2-carbonyl chloride with 2-amino-ethanesulfonic acid (1-isopropyl-piperidin-4-yl)-amide:

iv) 5-Chloro-thiophene-2-carboxylic acid [2-(1-isopropyl-piperidin-4-ylsulfamoyl)-ethyl]-amide 8.2 g (50.4 mmol) 5-chloro-thiophene-2-carboxylic acid were suspended in 26 ml (7 equiv.) thionyl chloride and the resulting mixture was refluxed for 1 h. The reaction mixture was concentrated under reduced pressure and the resulting residue was co-distilled three times with 150 ml toluene to give crude 9.64 g 5-chloro-thiophene-2-carbonyl chloride.

9.64 g (38.7 mmol) of above obtained crude 5-chloro-thiophene-2-carbonyl chloride were dissolved in 300 ml abs. dichloromethane and cooled to 4° C. At that temperature 8.5 ml (1.3 equiv.) DIPEA and a solution of 9.1 g (1.3 equiv.) 2-amino-ethanesulfonic acid (1-isopropyl-piperidin-4-yl)-amide in 20 ml dichloromethane were added. The reaction mixture was allowed to warm to room temperature. After 2 h, the reaction mixture was washed with 100 ml of a saturated NaHCO$_3$-solution. After phase separation the organic layer was dried over anhydrous MgSO$_4$ and concentrated under reduced pressure. Final purification by flash chromatography on silica gel (eluent: ethyl acetate/methanol) gave pure 5-chloro-thiophene-2-carboxylic acid [2-(1-isopropyl-piperidin-4-ylsulfamoyl)-ethyl]-amide as a colorless solid.

Yield: 8.5 g MS (ES$^+$): m/e=394, chloro pattern.

For 5-chloro-thiophene-2-carboxylic acid [2-(1-isopropyl-piperidin-4-ylsulfamoyl)-ethyl]-amide several crystalline salts could be obtained: for example a hydrochloride, fumarate, maleate, citrate.

The crystalline fumarate was prepared as following:

v) 5-Chloro-thiophene-2-carboxylic acid [2-(1-isopropyl-piperidin-4-ylsulfamoyl)-ethyl]-amide fumarate 300 mg (0.76 mmol) of pure 5-chloro-thiophene-2-carboxylic acid [2-(1-isopropyl-piperidin-4-ylsulfamoyl)-ethyl]-amide were dissolved in 1.5 ml acetone. 88.4 mg (1 equiv.) fumaric acid, dissolved in a mixture of 3 ml acetone and 0.1 ml water, were added dropwise. After 48 h the formed precipitate was filtered off and washed with 3 ml cold acetone. The filter residue was dried at 35° C. under vacuo to give crystalline 5-chloro-thiophene-2-carboxylic acid [2-(1-isopropyl-piperidin-4-ylsulfamoyl)-ethyl]-amide fumarate.

Yield: 226 mg.

Example 2

5-Chloro-thiophene-2-carboxylic acid [2-(1-cyclopropyl-piperidin-4-ylsulfamoyl)-ethyl]-amide i) 2-(1,3-Dioxo-1,3-dihydro-isoindol-2-yl)-ethanesulfonic acid (1-cyclopropyl-piperidin-4-yl)-amide 2-(1,3-Dioxo-1,3-dihydro-isoindol-2-yl)-ethanesulfonic acid (1-cyclopropyl-piperidin-4-yl)-amide was prepared by an analogous procedure as described for example 1 i) starting from 154 mg (1.1 mmol) 1-cyclopropyl-piperidin-4-ylamine (obtainable as described in EP 1479676) and 300 mg (1 equiv.) 2-(1,3-dioxo-1,3-dihydro-isoindol-2-yl)-ethanesulfonyl chloride. The product was obtained in crude form as a colorless foam.

Yield: 396 mg MS (ES$^+$): m/e=378.

ii) 2-Amino-ethanesulfonic acid (1-cyclopropyl-piperidin-4-yl)-amide

2-Amino-ethanesulfonic acid (1-cyclopropyl-piperidin-4-yl)-amide was prepared by an analogous procedure as described for example 1 ii) starting from 395 mg (1.05 mmol) crude 2-(1,3-dioxo-1,3-dihydro-isoindol-2-yl)-ethanesulfonic acid (1-cyclopropyl-piperidin-4-yl)-amide. The product was obtained as a colorless oil.

Yield: 429 mg MS (ES$^+$): m/e=248.

iii) 5-Chloro-thiophene-2-carboxylic acid [2-(1-cyclopropyl-piperidin-4-ylsulfamoyl)-ethyl]-amide 5-Chloro-thiophene-2-carboxylic acid [2-(1-cyclopropyl-piperidin-4-ylsulfamoyl)-ethyl]-amide was prepared by an analogous procedure as described in example 1 iii) starting from 339 mg (2 equiv.) 5-chloro-thiophene-2-carboxylic acid and 258 mg (1.04 mmol) 2-amino-ethanesulfonic acid (1-cyclopropyl-piperidin-4-yl)-amide. Final purification by preparative RP-HPLC (CH$_3$CN/H$_2$O gradient+0.1% TFA) gave pure 5-chloro-thiophene-2-carboxylic acid [2-(1-cyclopropyl-piperidin-4-ylsulfamoyl)-ethyl]-amide. The title compound was obtained as its trifluoroacetate in form of a colorless amorphous material.

Yield: 148 mg MS (ES$^+$): m/e=392, chloro pattern.

Example 3

5-Chloro-thiophene-2-carboxylic acid {2-[(1-isopropyl-piperidin-4-yl)-methyl-sulfamoyl]-ethyl}-amide i) (1-Isopropyl-piperidin-4-yl)-carbamic acid ethyl ester To a solution of 5.00 g (23.2 mmol) 1-isopropyl-piperidin-4-ylamine dihydrochloride and 12.88 ml (4 equiv.) triethylamine in 100 ml dichloromethane were added 2.22 ml (1 equiv.) ethyl chloroformate under temperature control.

The resulting mixture was stirred for 2.5 h at room temperature. After complete conversion the mixture was washed with 50 ml water. The organic phase was concentrated under vacuo to give crude (1-isopropyl-piperidin-4-yl)-carbamic acid ethyl ester as a colorless, crystalline material.

Yield: 4.15 g MS (ES$^+$): m/e=215.

ii) (1-Isopropyl-piperidin-4-yl)-methyl-amine 100 ml absolute diethyl ether were placed in a dry three-necked flask equipped with a condenser. 4.35 g LiAlH$_4$ (6 equiv.) were added and the mixture was stirred at room temperature under an argon atmosphere. Carefully, 4.10 g (19.13 mmol) (1-isopropyl-piperidin-4-yl)-carbamic acid ethyl ester were added portionwise and the resulting mixture was refluxed for 7 h. Since the conversion was not complete, 1.00 g (≈1.4 equiv.) LiAlH$_4$ was added and the mixture was refluxed for further 2 h. The reaction mixture was cooled and, carefully, 14 ml water were added dropwise over a 20-minute period. The mixture was diluted with 40 ml water and 50 ml diethyl ether. The phases were separated. The aqueous phase (suspension) was treated with a 10% NaOH-solution and washed twice with 100 ml diethyl ether. The organic phases were combined, dried over anhydrous $Na_2SO_4$ and concentrated under reduced pressure. The crude product was obtained as a colorless oil. Yield: 2.91 g MS (ES$^+$): m/e=157.

iii) 2-(1,3-Dioxo-1,3-dihydro-isoindol-2-yl)-ethanesulfonic acid (1-isopropyl-piperidin-4-yl)-methyl-amide 2-(1,3-Dioxo-1,3-dihydro-isoindol-2-yl)-ethanesulfonic acid (1-isopropyl-piperidin-4-yl)-methyl-amide was prepared by an analogous procedure as described for example 1 i) starting from 171.3 mg (1.1 mmol) (1-isopropyl-piperidin-4-yl)-methyl-amine and 300 mg (1 equiv.) 2-(1,3-dioxo-1,3-dihydro-isoindol-2-yl)-ethanesulfonyl chloride. 2-(1,3-Dioxo-1,3-dihydro-isoindol-2-yl)-ethanesulfonic acid (1-isopropyl-piperidin-4-yl)-methyl-amide was obtained as a light yellow foam. Yield: 385 mg MS (ES$^+$): m/e=394.

iv) 2-Amino-ethanesulfonic acid (1-isopropyl-piperidin-4-yl)-methyl-amide

2-Amino-ethanesulfonic acid (1-isopropyl-piperidin-4-yl)-methyl-amide was prepared by an analogous procedure as described for example 1 ii) starting from 385 mg (0.98 mmol) 2-(1,3-dioxo-1,3-dihydro-isoindol-2-yl)-ethanesulfonic acid (1-isopropyl-piperidin-4-yl)-methyl-amide. The product was obtained as a yellow oil. Yield: 482 mg MS (ES$^+$): m/e=264.

v) 5-Chloro-thiophene-2-carboxylic acid {2-[(1-isopropyl-piperidin-4-yl)-methyl-sulfamoyl]-ethyl}-amide 5-Chloro-thiophene-2-carboxylic acid {2-[(1-isopropyl-piperidin-4-yl)-methyl-sulfamoyl]-ethyl}-amide was prepared by an analogous procedure as described for example 1 iii) starting from 318 mg (2 equiv.) 5-chloro-thiophene-2-carboxylic acid and 258 mg (0.98 mmol) crude 2-amino-ethanesulfonic acid (1-isopropyl-piperidin-4-yl)-methyl-amide. Final purification was achieved by preparative RP-HPLC ($CH_3CN/H_2O$ gradient+0.1% TFA). After lyophilisation and transformation into its hydrochloride the title compound was obtained as a colorless, amorphous solid.

Yield: 103 mg MS (ES$^+$): m/e=408, chloro pattern.

Example 4

5-Chloro-thiophene-2-carboxylic acid {2-[(1-isopropyl-piperidin-4-yl)-(2,2,2-trifluoro-ethyl)-sulfamoyl]-ethyl}-amide i) 2-(1,3-Dioxo-1,3-dihydro-isoindol-2-yl)-ethanesulfonic acid (1-isopropyl-piperidin-4-yl)-(2,2,2-trifluoro-ethyl)-amide To a suspension of 448.2 mg (1.18 mmol) 2-(1,3-dioxo-1,3-dihydro-isoindol-2-yl)-ethanesulfonic acid (1-isopropyl-piperidin-4-yl)-amide and 489.7 mg (3 equiv.) $K_2CO_3$ in 6 ml DMF were added 603.0 mg (2.2 equiv.) 2,2,2-trifluoroethyl trifluoromethanesulfonate. The reaction mixture was stirred at room temperature. After 48 h (50% conversion) the mixture was diluted with 30 ml ethyl acetate and washed twice with 10 ml water and once with brine. The organic phase was dried over anhydrous $MgSO_4$ and concentrated under reduced pressure. Final purification was achieved by preparative RP-HPLC ($CH_3CN/H_2O$ gradient+0.1% TFA). The product was obtained as trifluoroacetate. Yield: 156 mg MS (ES$^+$): m/e=462.

ii) 2-Amino-ethanesulfonic acid (1-isopropyl-piperidin-4-yl)-(2,2,2-trifluoro-ethyl)-amide 156.0 mg (0.27 mmol) 2-(1,3-Dioxo-1,3-dihydro-isoindol-2-yl)-ethanesulfonic acid (1-isopropyl-piperidin-4-yl)-(2,2,2-trifluoro-ethyl)-amide were dissolved in 5 ml MeOH. 2.98 ml (22 equiv.) of a 2 M methylamine-solution in MeOH were added and the reaction mixture was stirred at room temperature for 20 h. The mixture was concentrated under reduced pressure to give crude 2-amino-ethanesulfonic acid (1-isopropyl-piperidin-4-yl)-(2,2,2-trifluoro-ethyl)-amide.

Yield: 90 mg MS (ES$^+$): m/e=332.

iii) 5-Chloro-thiophene-2-carboxylic acid {2-[(1-isopropyl-piperidin-4-yl)-(2,2,2-trifluoro-ethyl)-sulfamoyl]-ethyl}-amide 113.0 mg (0.34 mmol) crude 2-amino-ethanesulfonic acid (1-isopropyl-piperidin-4-yl)-(2,2,2-trifluoro-ethyl)-amide, 55.5 mg (1 equiv.) 5-chlorothiophene-2-carboxylic acid, 134.3 mg (1.2 equiv.) TOTU and 113.4 µl (2.4 equiv.) triethylamine were dissolved in 3 ml DMF and stirred at room temperature overnight. The reaction mixture was concentrated under reduced pressure and purified by preparative RP-HPLC ($CH_3CN/H_2O$ gradient+0.1% TFA). The product was obtained as trifluoroacetate in form of a white, amorphous material.

Yield: 70 mg MS (ES$^+$): m/e=476, chloro pattern.

Example 5

5-Chloro-thiophene-2-carboxylic acid [2-(3,4,5,6-tetrahydro-2H-[1,4']bipyridinyl-4-ylsulfamoyl)-ethyl]-amide i) 2-(1,3-Dioxo-1,3-dihydro-isoindol-2-yl)-ethanesulfonic acid (3,4,5,6-tetrahydro-2H-[1,4']bipyridinyl-4-yl)-amide 2-(1,3-Dioxo-1,3-dihydro-isoindol-2-yl)-ethanesulfonic acid (3,4,5,6-tetrahydro-2H[1,4']bipyridinyl-4-yl)-amide was prepared by an analogous procedure as described for example 1 i) starting from 638 mg (3.6 mmol) 3,4,5,6-tetrahydro-2H-[1,4']bipyridinyl-4-ylamine and 985 mg (1 equiv.) 2-(1,3-dioxo-1,3-dihydro-isoindol-2-yl)-ethanesulfonyl chloride. The product was obtained in crude form as a light yellow foam. Yield: 860 mg MS (ES$^+$): m/e=415.

ii) 2-Amino-ethanesulfonic acid (3,4,5,6-tetrahydro-2H-[1,4']bipyridinyl-4-yl)-amide 2-Amino-ethanesulfonic acid (3,4,5,6-tetrahydro-2H-[1,4']bipyridinyl-4-yl)-amide was prepared by an analogous procedure as described for example 1 ii) starting from 860 mg (2.08 mmol) crude 2-(1,3-dioxo-1,3-dihydro-isoindol-2-yl)-ethanesulfonic acid (3,4,5,6-tetrahydro-2H-[1,4']bipyridinyl-4-yl)-amide. The product was obtained as a colorless oil.

Yield: 590 mg MS (ES$^+$): m/e=285.

iii) 5-Chloro-thiophene-2-carboxylic acid [2-(3,4,5,6-tetrahydro-2H-[1,4']bipyridinyl-4-ylsulfamoyl)-ethyl]-amide To a solution of 337 mg (1.0 equiv.) 5-chloro-thiophene-2-carboxylic acid in 10 ml DMF were added 789 mg (1.0 equiv.) HATU and 706 µl (2 equiv.) DIPEA. The resulting mixture was stirred for 30 min at room temperature. Subsequently a solution of 590 mg (2.08 mmol) 2-amino-ethanesulfonic acid (3,4,5,6-tetrahydro-2H-[1,4']bipyridinyl-4-yl)-amide and 353 µl (1 equiv.) DIPEA in 5 ml DMF was added. The resulting mixture was stirred at room temperature overnight and then concentrated under reduced pressure. The resulting residue was taken up in 10 ml dichloromethane and washed with a saturated NaHCO$_3$-solution and with brine. The organic phase was dried over anhydrous MgSO$_4$ and concentrated under reduced pressure. Final purification was achieved by preparative RP-HPLC (CH$_3$CN/H$_2$O gradient+ 0.1% TFA). The title compound was obtained as its trifluoroacetate in form of a colorless amorphous material.

Yield: 250 mg MS (ES$^+$): m/e=429, chloro pattern.

Example 6

5-Chloro-thiophene-2-carboxylic acid[2-(azetidin-3-ylsulfamoyl)-ethyl]-amide i) 3-[2-(1,3-Dioxo-1,3-dihydro-isoindol-2-yl)-ethanesulfonylamino]-azetidine-1-carboxylic acid tert-butyl ester 3-[2-(1,3-Dioxo-1,3-dihydro-isoindol-2-yl)-ethanesulfonylamino]-azetidine-1-carboxylic acid tert-butyl ester was prepared by an analogous procedure as described for example 1 i) starting from 189 mg (1.1 mmol) 3-amino-azetidine-1-carboxylic acid tert-butyl ester and 300 mg (1 equiv.) 2-(1,3-dioxo-1,3-dihydro-isoindol-2-yl)-ethanesulfonyl chloride. The product was obtained in crude form as light yellow foam. Yield: 480 mg MS (ES$^+$): m/e=410.

ii) 3-(2-Amino-ethanesulfonylamino)-azetidine-1-carboxylic acid tert-butyl ester 3-(2-Amino-ethanesulfonylamino)-azetidine-1-carboxylic acid tert-butyl ester was prepared by an analogous procedure as described for example 1 ii) starting from 448 mg (1.1 mmol) crude 3-[2-(1,3-dioxo-1,3-dihydro-isoindol-2-yl)-ethanesulfonylamino]-azetidine-1-carboxylic acid tert-butyl ester. The product was obtained as a colorless oil.

Yield: 412 mg MS (ES$^+$): m/e=280.

iii) 3-{2-[(5-Chloro-thiophene-2-carbonyl)-amino]-ethanesulfonylamino}-azetidine-1-carboxylic acid tert-butyl ester 3-{2-[(5-Chloro-thiophene-2-carbonyl)-amino]-ethanesulfonylamino}-azetidine-1-carboxylic acid tert-butyl ester was prepared by an analogous procedure as described in example 5 iii) starting from 240 mg (1.3 equiv.) 5-chloro-thiophene-2-carboxylic acid and 308 mg (1.1 mmol) 3-(2-amino-ethanesulfonylamino)-azetidine-1-carboxylic acid tert-butyl ester. Final purification by preparative RP-HPLC (CH$_3$CN/H$_2$O gradient+0.1% TFA) gave pure 3-{2-[(5-chloro-thiophene-2-carbonyl)-amino]-ethanesulfonylamino}-azetidine-1-carboxylic acid tert-butyl ester. The title compound was obtained in form of a colorless amorphous material.

Yield: 200 mg MS (ES$^+$): m/e=424, chloro pattern.

iv) 5-Chloro-thiophene-2-carboxylic acid [2-(azetidin-3-ylsulfamoyl)-ethyl]-amide 200 mg (0.47 mmol) 3-{2-[(5-Chloro-thiophene-2-carbonyl)-amino]-ethanesulfonylamino}-azetidine-1-carboxylic acid tert-butyl ester were dissolved in 10 ml of a 4 M HCl-solution in dioxane. After stirring at room temperature for 24 h the reaction mixture was concentrated under reduced pressure. The residue was digerated with CH$_3$CN, filtered and washed twice with CH$_3$CN. After drying at 40° C. overnight the title compound was isolated as its hydrochloride in form of a colorless crystalline material. Yield: 138 mg MS (ES$^+$): m/e=324, chloro pattern.

Example 7

5-Chloro-thiophene-2-carboxylic acid [2-(1-isopropyl-azetidin-3-ylsulfamoyl)-ethyl]-amide 85.3 mg (5 equiv.) 2-Bromo-propane were added to a mixture of 50 mg (0.14 mmol) 5-chloro-thiophene-2-carboxylic acid[2-(azetidin-3-ylsulfamoyl)-ethyl]-amide hydrochloride and 38 mg (2 equiv.) K$_2$CO$_3$ in 5 ml DMF. The resulting mixture was stirred for 2 h at 70° C., then diluted with 15 ml dichloromethane and washed with 3 ml of a saturated NaHCO$_3$-solution. The organic phase was dried over anhydrous MgSO$_4$ and concentrated under reduced pressure. Final purification by preparative RP-HPLC (CH$_3$CN/H$_2$O gradient+0.1% TFA) gave pure 5-chloro-thiophene-2-carboxylic acid [2-(1-isopropyl-azetidin-3-ylsulfamoyl)-ethyl]-amide. The title compound was obtained as its trifluoroacetate in form of a colorless amorphous material.

Yield: 8 mg MS (ES$^+$): m/e=366, chloro pattern.

Example 8

5-Chloro-thiophene-2-carboxylic acid [2-(4-benzyl-piperazin-1-ylsulfamoyl)-ethyl]-amide i) 2-(1,3-Dioxo-1,3-dihydro-isoindol-2-yl)-ethanesulfonic acid (4-benzyl-piperazin-1-yl)-amide 2-(1,3-Dioxo-1,3-dihydro-isoindol-2-yl)-ethanesulfonic acid (4-benzyl-piperazin-1-yl)-amide was prepared by an analogous procedure as described for example 1 i) starting from 140 mg (0.73 mmol) 4-benzyl-piperazin-1-ylamine and 200 mg (1 equiv.) 2-(1,3-dioxo-1,3-dihydro-isoindol-2-yl)-ethanesulfonyl chloride. The product was obtained in crude form as a light yellow foam.

Yield: 323 mg MS (ES$^+$): m/e=429.

ii) 2-Amino-ethanesulfonic acid (4-benzyl-piperazin-1-yl)-amide

2-Amino-ethanesulfonic acid (4-benzyl-piperazin-1-yl)-amide was prepared by an analogous procedure as described for example 1 ii) starting from 313 mg (0.73 mmol) crude 2-(1,3-dioxo-1,3-dihydro-isoindol-2-yl)-ethanesulfonic acid (4-benzyl-piperazin-1-yl)-amide. The product was obtained as colorless oil.

Yield: 183 mg MS (ES$^+$): m/e=299.

iii) 5-Chloro-thiophene-2-carboxylic acid [2-(4-benzyl-piperazin-1-ylsulfamoyl)-ethyl]-amide 5-Chloro-thiophene-2-carboxylic acid [2-(4-benzyl-piperazin-1-ylsulfamoyl)-ethyl]-amide was prepared by an analogous procedure as described in example 5 iii) starting from 100 mg (1 equiv.) 5-chloro-thiophene-2-carboxylic acid and 183 mg (0.61 mmol) 2-amino-ethanesulfonic acid (4-benzyl-piperazin-1-yl)-amide. Final purification by preparative RP-HPLC (CH$_3$CN/H$_2$O gradient+0.1% TFA) gave pure 5-chloro-thiophene-2-carboxylic acid [2-(4-benzyl-piperazin-1-ylsulfamoyl)-ethyl]-amide. The title compound was obtained as its trifluoroacetate in form of a colorless amorphous material. Yield: 41 mg MS (ES$^+$): m/e=443, chloro pattern.

Example 9

5-Bromo-thiophene-2-carboxylic acid[2-(1-isopropyl-piperidin-4-ylsulfamoyl)-ethyl]-amide To a solution of 137 mg (1.1 equiv.) 5-bromo-thiophene-2-carboxylic acid in 3 ml DMF were added 251 mg (1.1 equiv.) HATU and 306 µl (3 equiv.) DIPEA. The resulting mixture was stirred for 30 min at room temperature. Subsequently a solution of 150 mg (0.60 mmol) 2-amino-ethanesulfonic acid (1-isopropyl-piperidin-4-yl)-amide and 102 µl (1 equiv.) DIPEA in 2 ml DMF was added. The resulting mixture was stirred at room temperature overnight and then concentrated under reduced pressure. The resulting residue was taken up in 10 ml dichloromethane and washed with a saturated NaHCO$_3$-solution and with brine. The organic phase was dried over anhydrous MgSO$_4$ and concentrated under reduced pressure. Final purification was achieved by preparative RP-HPLC (CH$_3$CN/H$_2$O gradient+0.1% TFA). The product was obtained as trifluoroacetate.

Yield: 152 mg MS (ES$^+$): m/e=438, bromo pattern.

Example 10

5-Methyl-thiophene-2-carboxylic acid [2-(1-isopropyl-piperidin-4-ylsulfamoyl)-ethyl]-amide 5-Methyl-thiophene-2-carboxylic acid [2-(1-isopropyl-piperidin-4-ylsulfamoyl)-ethyl]-amide was prepared by an analogous procedure as described in example 9 starting from 94 mg (1.1 equiv.) 5-methyl-thiophene-2-carboxylic acid and 150 mg (0.60 mmol) 2-amino-ethanesulfonic acid (1-isopropyl-piperidin-4-yl)-amide. Final purification by preparative RP-HPLC (CH$_3$CN/H$_2$O gradient+0.1% TFA) gave pure 5-methyl-thiophene-2-carboxylic acid [2-(1-isopropyl-piperidin-4-ylsulfamoyl)-ethyl]-amide. The title compound was obtained as its trifluoroacetate in form of a colorless amorphous material, which turned out to be hygroscopic with time.

Yield: 140 mg MS (ES$^+$): m/e=374.

Example 11

5-Bromo-furan-2-carboxylic acid [2-(1-isopropyl-piperidin-4-ylsulfamoyl)-ethyl]-amide 5-Bromo-furan-2-carboxylic acid [2-(1-isopropyl-piperidin-4-ylsulfamoyl)-ethyl]-amide was prepared by an analogous procedure as described in example 9 starting from 126 mg (1.1 equiv.) 5-bromo-furan-2-carboxylic acid and 150 mg (0.60 mmol) 2-amino-ethanesulfonic acid (1-isopropyl-piperidin-4-yl)-amide. Final purification by preparative RP-HPLC (CH$_3$CN/H$_2$O gradient+0.1% TFA) gave pure 5-bromo-furan-2-carboxylic acid [2-(1-isopropyl-piperidin-4-ylsulfamoyl)-ethyl]-amide. The title compound was obtained as its trifluoroacetate in form of a colorless amorphous material. Yield: 121 mg MS (ES$^+$): m/e=422, bromo pattern.

Example 12

4-Chloro-N-[2-(1-isopropyl-piperidin-4-ylsulfamoyl)-ethyl]-benzamide

4-Chloro-N-[2-(1-isopropyl-piperidin-4-ylsulfamoyl)-ethyl]-benzamide was prepared by an analogous procedure as described in example 9 starting from 104 mg (1.1 equiv.) 4-chloro-benzoic acid and 150 mg (0.60 mmol) 2-amino-ethanesulfonic acid (1-isopropyl-piperidin-4-yl)-amide. Final purification by preparative RP-HPLC (CH$_3$CN/H$_2$O gradient+0.1% TFA) gave pure 4-chloro-N-[2-(1-isopropyl-piperidin-4-ylsulfamoyl)-ethyl]-benzamide. The title compound was obtained as its trifluoroacetate in form of a colorless amorphous material.

Yield: 90 mg MS (ES$^+$): m/e=388, chloro pattern.

Example 13

5-Chloro-pyridine-2-carboxylic acid [2-(1-isopropyl-piperidin-4-ylsulfamoyl)-ethyl]-amide 5-Chloro-pyridine-2-carboxylic acid[2-(1-isopropyl-piperidin-4-ylsulfamoyl)-ethyl]-amide was prepared by an analogous procedure as described in example 9 starting from 104 mg (1.1 equiv.) 5-chloro-pyridine-2-carboxylic acid and 150 mg (0.60 mmol) 2-amino-ethanesulfonic acid (1-isopropyl-piperidin-4-yl)-amide. Final purification by preparative RP-HPLC (CH$_3$CN/H$_2$O gradient+0.1% TFA) gave pure 5-chloro-pyridine-2-carboxylic acid [2-(1-isopropyl-piperidin-4-ylsulfamo-yl)-ethyl]-amide. The title compound was obtained as its trifluoroacetate in form of a colorless amorphous material. Yield: 60 mg MS (ES$^+$): m/e=389, chloro pattern.

Example 14

3-Chloro-N-[2-(1-isopropyl-piperidin-4-ylsulfamoyl)-ethyl]-benzamide

3-Chloro-N-[2-(1-isopropyl-piperidin-4-ylsulfamoyl)-ethyl]-benzamide was prepared by an analogous procedure as described in example 9 starting from 104 mg (1.1 equiv.) 3-chloro-benzoic acid and 150 mg (0.60 mmol) 2-amino-ethanesulfonic acid (1-isopropyl-piperidin-4-yl)-amide. Final purification by preparative RP-HPLC (CH$_3$CN/H$_2$O gradient+0.1% TFA) gave pure 3-chloro-N-[2-(1-isopropyl-piperidin-4-ylsulfamoyl)-ethyl]-benzamide. The title compound was obtained as its trifluoroacetate in form of a colorless amorphous material.

Yield: 133 mg MS (ES$^+$): m/e=388, chloro pattern.

Example 15

5-Chloro-thiophene-2-carboxylic acid {2-[(1-isopropyl-piperidin-4-yl)-(2-methoxy-ethyl)-sulfamoyl]-ethyl}-amide 215 µl (1 equiv.) 1-Bromo-2-methoxy-ethane were added to a mixture of 900 mg (2.29 mol) 5-chloro-thiophene-2-carboxylic acid [2-(1-isopropyl-piperidin-4-ylsulfamoyl)-ethyl]-amide and 1.49 g (2 equiv.) Cs$_2$CO$_3$ in 25 ml DMF. The resulting mixture was stirred for 7 h at 80° C. Further 372 mg (0.5 equiv.) Cs$_2$CO$_3$ and 107 µl (0.5 equiv.) 1-bromo-2-methoxy-ethane were added and the reaction mixture was stirred for another 7 h at 80° C. After the reaction had been completed the mixture was filtered and concentrated under reduced pressure. Final purification by preparative RP-HPLC (CH₃CN/H₂O gradient+0.1% TFA) gave pure 5-chloro-thiophene-2-carboxylic acid {2-[(1-isopropyl-piperidin-4-yl)-(2-methoxy-ethyl)-sulfamoyl]-ethyl}-amide as its trifluoroacetate. The product was taken up in dichloromethane and treated with a saturated NaHCO₃-solution. After phase separation the organic phase was concentrated and the resulting residue was dissolved in water containing 1 equiv. of fumaric acid. Lyophilisation gave the title compound as its fumarate in form of a colorless amorphous material.

Yield: 800 mg MS (ES⁺): m/e=452, chloro pattern.

Example 16

5-Chloro-thiophene-2-carboxylic acid {2-[(2-hydroxy-ethyl)-(1-isopropyl-piperidin-4-yl)-sulfamoyl]-ethyl}-amide i) 5-Chloro-thiophene-2-carboxylic acid {2-[[2-(tert-butyl-dimethyl-silanyloxy)-ethyl]-(1-isopropyl-piperidin-4-yl)-sulfamoyl]-ethyl}-amide 5-Chloro-thiophene-2-carboxylic acid {2-[[2-(tert-butyl-dimethyl-silanyloxy)-ethyl]-(1-isopropyl-piperidin-4-yl)-sulfamoyl]-ethyl}-amide was prepared by an analogous procedure as described in example 15 starting from 2.3 ml (3.5 equiv.) (2-bromo-ethoxy)-tert-butyl-dimethyl-silane and 1.2 g (3.05 mmol) 5-chloro-thiophene-2-carboxylic acid [2-(1-isopropyl-piperidin-4-ylsulfamoyl)-ethyl]-amide. 5-Chloro-thiophene-2-carboxylic acid {2-[[2-(tert-butyl-dimethyl-silanyloxy)-ethyl]-(1-isopropyl-piperidin-4-yl)-sulfamoyl]-ethyl}-amide was obtained as crude material which was pure enough for further transformations.

Yield: 1.65 g MS (ES⁺): m/e=552, chloro pattern.

ii) 5-Chloro-thiophene-2-carboxylic acid {2-[(2-hydroxy-ethyl)-(1-isopropyl-piperidin-4-yl)-sulfamoyl]-ethyl}-amide 1.65 g (2.99 mmol) of crude 5-chloro-thiophene-2-carboxylic acid {2-[[2-(tert-butyl-dimethyl-silanyloxy)-ethyl]-(1-isopropyl-piperidin-4-yl)-sulfamoyl]-ethyl}-amide were dissolved in 50 ml methanol. 6 ml of a 1M aqueous HCl-solution were added and the resulting mixture was stirred for 48 h at room temperature. The mixture was concentrated under reduced pressure. Final purification by preparative RP-HPLC (CH₃CN/H₂O gradient+0.1% TFA) gave pure 5-chloro-thiophene-2-carboxylic acid {2-[(2-hydroxy-ethyl)-(1-isopropyl-piperidin-4-yl)-sulfamoyl]-ethyl}-amide as its trifluoroacetate. The product was taken up in dichloromethane and treated with a saturated NaHCO₃-solution. After phase separation the organic phase was concentrated and the resulting residue was dissolved in water containing 1 equiv. of fumaric acid. Lyophilisation gave the title compound as its fumarate in form of a colorless amorphous material.

Yield: 480 mg MS (ES⁺): m/e=438, chloro pattern.

Example 17

5-Chloro-thiophene-2-carboxylic acid {2-[(3-hydroxy-propyl)-(1-isopropyl-piperidin-4-yl)-sulfamoyl]-ethyl}-amide i) 5-Chloro-thiophene-2-carboxylic acid (2-{(1-isopropyl-piperidin-4-yl)-[3-(tetrahydro-pyran-2-yloxy)-propyl]-sulfamoyl}-ethyl)-amide 5-Chloro-thiophene-2-carboxylic acid (2-{(1-isopropyl-piperidin-4-yl)-[3-(tetrahydro-pyran-2-yloxy)-propyl]-sulfamoyl}-ethyl)-amide was prepared by an analogous procedure as described in example 15 starting from 245 mg (1.5 equiv.) 2-(3-chloro-propoxy)-tetrahydro-pyran and 360 mg (0.91 mmol) 5-chloro-thiophene-2-carboxylic acid [2-(1-isopropyl-piperidin-4-ylsulfamoyl)-ethyl]-amide. Final purification by preparative RP-HPLC (CH₃CN/H₂O gradient+0.05% formic acid) gave pure 5-chloro-thiophene-2-carboxylic acid (2-{(1-isopropyl-piperidin-4-yl)-[3-(tetrahydro-pyran-2-yloxy)-propyl]-sulfamoyl}-ethyl)-amide as its formate.

Yield: 220 mg MS (ES⁺): m/e=536, chloro pattern.

ii) 5-Chloro-thiophene-2-carboxylic acid {2-[(3-hydroxy-propyl)-(1-isopropyl-piperidin-4-yl)-sulfamoyl]-ethyl}-amide 220 mg (0.38 mmol) 5-Chloro-thiophene-2-carboxylic acid (2-{(1-isopropyl-piperidin-4-yl)-[3-(tetrahydro-pyran-2-yloxy)-propyl]-sulfamoyl}-ethyl)-amide were dissolved in a mixture of 4 ml THF, 8 ml conc. acetic acid and 2 ml water. The resulting mixture was stirred for 8 h at 60° C., concentrated under reduced pressure and purified by preparative RP-HPLC (CH₃CN/H₂O gradient+0.1% TFA). The product was taken up in dichloromethane and treated with a saturated NaHCO₃-solution. After phase separation the organic phase was concentrated and the resulting residue was dissolved in water containing 1 equiv. of fumaric acid. Lyophilisation gave the title compound as its fumarate in form of a colorless amorphous material.

Yield: 170 mg MS (ES⁺): m/e=452, chloro pattern.

Example 18

5-Chloro-thiophene-2-carboxylic acid {2-[dimethylcarbamoylmethyl-(1-isopropyl-piperidin-4-yl)-sulfamoyl]-ethyl}-amide 5-Chloro-thiophene-2-carboxylic acid {2-[dimethylcarbamoylmethyl-(1-isopropyl-piperidin-4-yl)-sulfamoyl]-ethyl}-amide was prepared by an analogous procedure as described in example 15 starting from 0.8 ml (2 equiv.) 2-chloro-N,N-dimethyl-acetamide and 1.5 g (3.81 mmol) 5-chloro-thiophene-2-carboxylic acid [2-(1-isopropyl-piperidin-4-ylsulfamoyl)-ethyl]-amide. Final purification by preparative RP-HPLC (CH₃CN/H₂O gradient+0.1% TFA) gave pure 5-chloro-thiophene-2-carboxylic acid {2-[dimethylcarbamoylmethyl-(1-isopropyl-piperidin-4-yl)-sulfamoyl]-ethyl}-amide as its trifluoroacetate. The product was taken up in dichloromethane and treated with a saturated NaHCO₃-solution.

After phase separation the organic phase was concentrated and the resulting residue was dissolved in water containing 1 equiv. of fumaric acid. Lyophilisation gave the title compound as its fumarate in form of a colorless amorphous material.

Yield: 485 mg MS (ES⁺): m/e=479, chloro pattern.

Example 19

5-Chloro-thiophene-2-carboxylic acid {2-[(1-isopropyl-piperidin-4-yl)-(2-morpholin-4-yl-2-oxo-ethyl)-sulfamoyl]-ethyl}-amide 5-Chloro-thiophene-2-carboxylic acid {2-[(1-isopropyl-piperidin-4-yl)-(2-morpholin-4-yl-2-oxo-ethyl)-sulfamoyl]-ethyl}-amide was prepared by an analogous procedure as described in example 15 starting from 83 mg (2 equiv.)

2-chloro-1-morpholin-4-yl-ethanone and 100 mg (0.25 mmol) 5-chloro-thiophene-2-carboxylic acid [2-(1-isopropyl-piperidin-4-ylsulfamoyl)-ethyl]-amide. Final purification by preparative RP-HPLC (CH$_3$CN/H$_2$O gradient+0.1% TFA) gave pure 5-chloro-thiophene-2-carboxylic acid {2-[(1-isopropyl-piperidin-4-yl)-(2-morpholin-4-yl-2-oxo-ethyl)-sulfamoyl]-ethyl}-amide. The title compound was obtained as its trifluoroacetate in form of a colorless amorphous material, which turned out to be hygroscopic with time.
Yield: 70 mg MS (ES$^+$): m/e=521, chloro pattern.

Example 20

5-Chloro-thiophene-2-carboxylic acid {2-[carbamoylmethyl-(1-isopropyl-piperidin-4-yl)-sulfamoyl]-ethyl}-amide 5-Chloro-thiophene-2-carboxylic acid {2-[carbamoylmethyl-(1-isopropyl-piperidin-4-yl)-sulfamoyl]-ethyl}-amide was prepared by an analogous procedure as described in example 15 starting from 48 mg (2 equiv.) 2-chloro-acetamide and 100 mg (0.25 mmol) 5-chloro-thiophene-2-carboxylic acid [2-(1-isopropyl-piperidin-4-ylsulfamoyl)-ethyl]-amide. Final purification by preparative RP-HPLC (CH$_3$CN/H$_2$O gradient+0.1% TFA) gave pure 5-chloro-thiophene-2-carboxylic acid {2-[carbamoylmethyl-(1-isopropyl-piperidin-4-yl)-sulfamoyl]-ethyl}-amide. The title compound was obtained as its trifluoroacetate in form of a colorless amorphous material.
Yield: 38 mg MS (ES$^+$): m/e=451, chloro pattern.

Example 21

5-Chloro-thiophene-2-carboxylic acid {2-[(1-isopropyl-piperidin-4-yl)-(5-methyl-isoxazol-3-ylmethyl)-sulfamoyl]-ethyl}-amide 5-Chloro-thiophene-2-carboxylic acid {2-[(1-isopropyl-piperidin-4-yl)-(5-methyl-isoxazol-3-ylmethyl)-sulfamoyl]-ethyl}-amide was prepared by an analogous procedure as described in example 15 starting from 67 mg (1 equiv.) 3-chloromethyl-5-methyl-isoxazole and 200 mg (0.50 mmol) 5-chloro-thiophene-2-carboxylic acid [2-(1-isopropyl-piperidin-4-ylsulfamoyl)-ethyl]-amide (reaction temperature: 60° C.). Final purification by preparative RP-HPLC (CH$_3$CN/H$_2$O gradient+0.1% TFA) gave pure 5-chloro-thiophene-2-carboxylic acid {2-[(1-isopropyl-piperidin-4-yl)-(5-methyl-isoxazol-3-ylmethyl)-sulfamoyl]-ethyl}-amide. The title compound was obtained as its trifluoroacetate in form of a colorless amorphous material.
Yield: 148 mg MS (ES$^+$): m/e=489, chloro pattern.

Example 22

5-Chloro-thiophene-2-carboxylic acid {2-[(1-isopropyl-piperidin-4-yl)-pyridin-3-ylmethyl-sulfamoyl]-ethyl}-amide 5-Chloro-thiophene-2-carboxylic acid {2-[(1-isopropyl-piperidin-4-yl)-pyridin-3-ylmethyl-sulfamoyl]-ethyl}-amide was prepared by an analogous procedure as described in example 15 starting from 83 mg (1 equiv.) 3-chloromethyl-pyridine hydrochloride and 200 mg (0.50 mmol) 5-chloro-thiophene-2-carboxylic acid [2-(1-isopropyl-piperidin-4-yl-sulfamoyl)-ethyl]-amide (reaction temperature: 60° C.). Final purification by preparative RP-HPLC (CH$_3$CN/H$_2$O gradient+0.1% TFA) gave pure 5-chloro-thiophene-2-carboxylic acid {2-[(1-isopropyl-piperidin-4-yl)-pyridin-3-ylmethyl-sulfamoyl]-ethyl}-amide. The title compound was obtained as its trifluoroacetate in form of a light yellow amorphous material.
Yield: 64 mg MS (ES$^+$): m/e=485, chloro pattern.

Example 23

5-Chloro-thiophene-2-carboxylic acid {2-[(1-isopropyl-piperidin-4-yl)-thiazol-2-ylmethyl-sulfamoyl]-ethyl}-amide i) (1-Isopropyl-piperidin-4-yl)-thiazol-2-ylmethyl-amine Under argon 185 µl (1 equiv.) thiazole-2-carbaldehyde were added to a solution of 300 mg (2.10 mmol) 1-isopropyl-piperidin-4-ylamine in 30 ml abs. dichloromethane. The resulting solution was cooled to 0° C. 60 µl (0.5 equiv.) conc. acetic acid were added and the mixture was stirred for 15 minutes at that temperature. Then, 491 mg (1.1 equiv.) sodium triacetoxyborohydride were added and the reaction mixture was stirred for 48 h at room temperature. After the reaction had been completed a few drops of water were added and the mixture was washed with a saturated NaHCO$_3$-solution. After phase separation the organic phase was concentrated under reduced pressure. The product was obtained in crude form as a yellow oil.
Yield: 217 mg MS (ES$^+$): m/e=240.

ii) 2-(1,3-Dioxo-1,3-dihydro-isoindol-2-yl)-ethanesulfonic acid (1-isopropyl-piperidin-4-yl)-thiazol-2-ylmethyl-amide 2-(1,3-Dioxo-1,3-dihydro-isoindol-2-yl)-ethanesulfonic acid (1-isopropyl-piperidin-4-yl)-thiazol-2-ylmethyl-amide was prepared by an analogous procedure as described for example 1 i) starting from 217 mg (0.91 mmol) (1-isopropyl-piperidin-4-yl)-thiazol-2-ylmethyl-amine and 250 mg (1 equiv.) 2-(1,3-dioxo-1,3-dihydro-isoindol-2-yl)-ethanesulfonyl chloride. Purification by flash chromatography on silica gel (eluent: CH$_2$Cl$_2$/MeOH) gave pure 2-(1,3-dioxo-1,3-dihydro-isoindol-2-yl)-ethanesulfonic acid (1-isopropyl-piperidin-4-yl)-thiazol-2-ylmethyl-amide as a light yellow foam. Yield: 178 mg MS (ES$^+$): m/e=477.

iii) 2-Amino-ethanesulfonic acid (1-isopropyl-piperidin-4-yl)-thiazol-2-ylmethyl-amide 2-Amino-ethanesulfonic acid (1-isopropyl-piperidin-4-yl)-thiazol-2-ylmethyl-amide was prepared by an analogous procedure as described for example 1 ii) starting from 178 mg (0.37 mmol) 2-(1,3-dioxo-1,3-dihydro-isoindol-2-yl)-ethanesulfonic acid (1-isopropyl-piperidin-4-yl)-thiazol-2-ylmethyl-amide and 0.75 ml (2 equiv.) of a 1M hydrazine-solution in THF. The product was obtained as brown oil.
Yield: 140 mg MS (ES$^+$): m/e=347.

iv) 5-Chloro-thiophene-2-carboxylic acid {2-[(1-isopropyl-piperidin-4-yl)-thiazol-2-ylmethyl-sulfamoyl]-ethyl}-amide 5-Chloro-thiophene-2-carboxylic acid {2-[(1-isopropyl-piperidin-4-yl)-thiazol-2-ylmethyl-sulfamoyl]-ethyl}-amide was prepared by an analogous procedure as described in example 5 iii) starting from 61 mg (1 equiv.) 5-chloro-thiophene-2-carboxylic acid and 129 mg (0.37 mmol)

2-amino-ethanesulfonic acid (1-isopropyl-piperidin-4-yl)-thiazol-2-ylmethyl-amide. Final purification by preparative RP-HPLC (CH$_3$CN/H$_2$O gradient+0.05% formic acid) gave pure 5-chloro-thiophene-2-carboxylic acid {2-[(1-isopropyl-piperidin-4-yl)-thiazol-2-ylmethyl-sulfamoyl]-ethyl}-amide. The title compound was obtained as its formate in form of a light brown amorphous material.

Yield: 66 mg MS (ES$^+$): m/e=491, chloro pattern.

Example 24

5-Chloro-thiophene-2-carboxylic acid {2-[(1-isopropyl-piperidin-4-yl)-propylaminocarbonyl-sulfamoyl]-ethyl}-amide

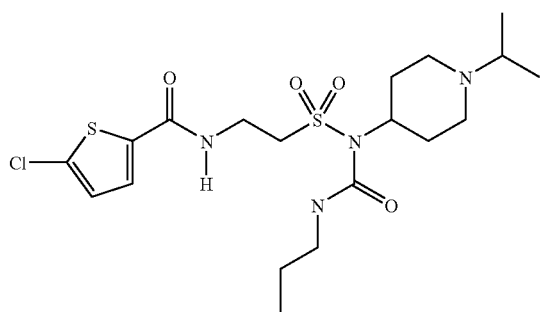

To a solution of 200 mg (0.50 mmol) 5-chloro-thiophene-2-carboxylic acid [2-(1-isopropyl-piperidin-4-ylsulfamoyl)-ethyl]-amide in 3 ml dichloromethane were added 0.1 ml (2 equiv.) 1-isocyanato-propane and 6 mg DMAP. The reaction mixture was stirred overnight at room temperature. The next day further 0.1 ml (2 equiv.) 1-isocyanato-propane and 6 mg DMAP were added. After stirring for 48 h at room temperature, the reaction mixture was washed with 3 ml water and concentrated under reduced pressure. Final purification by preparative RP-HPLC (CH$_3$CN/H$_2$O gradient+0.1% TFA) gave pure 5-chloro-thiophene-2-carboxylic acid {2-[(1-isopropyl-piperidin-4-yl)-propylaminocarbonyl-sulfamoyl]-ethyl}-amide. The title compound was obtained as its trifluoroacetate in form of a colorless amorphous material.

Yield: 12 mg MS (ES$^+$): m/e=479, chloro pattern.

Example 25

5-Chloro-thiophene-2-carboxylic acid {2-[acetyl-(1-isopropyl-piperidin-4-yl)-sulfamoyl]-ethyl}-amide To a solution of 800 mg (2.03 mmol) 5-chloro-thiophene-2-carboxylic acid [2-(1-isopropyl-piperidin-4-ylsulfamoyl)-ethyl]-amide in 20 ml dichloromethane were added sequentially 1.0 ml (5 equiv.) acetanhydride, 0.8 ml (5 equiv.) pyridine and 50 mg DMAP. The reaction mixture was stirred overnight at room temperature. The next day further 1.5 ml (7.5 equiv.) acetanhydride, 1.2 ml (7.5 equiv.) pyridine and 75 mg DMAP were added. The reaction mixture was stirred for 12 h under reflux and for further 12 h at room temperature. After complete conversion the reaction mixture was concentrated under reduced pressure. Final purification by preparative RP-HPLC (CH$_3$CN/H$_2$O gradient+0.1% TFA) gave pure 5-chloro-thiophene-2-carboxylic acid {2-[acetyl-(1-isopropyl-piperidin-4-yl)-sulfamoyl]-ethyl}-amide as its trifluoroacetate. The product was taken up in dichloromethane and treated with a saturated NaHCO$_3$-solution. After phase separation the organic phase was concentrated and the resulting residue was dissolved in water containing 1 equiv. of fumaric acid. Lyophilisation gave the title compound as its fumarate in form of a colorless amorphous material. Yield: 378 mg MS (ES$^+$): m/e=436, chloro pattern.

Example 26

5-Chloro-thiophene-2-carboxylic acid [2-(1-isopropyl-piperidin-4-ylsulfamoyl)-propyl]-amide i) Methanesulfonic acid 2-tert-butoxycarbonylamino-1-methyl-ethyl ester 8.24 g (47.0 mmol) (2-Hydroxy-propyl)-carbamic acid tert-butyl ester were dissolved in 100 ml dichloromethane. 7.8 ml (1.2 equiv.) triethylamine were added and the mixture was cooled to 0° C. At that temperature 4.37 ml (1.2 equiv.) methanesulfonyl chloride were added dropwise. The resulting solution was allowed to reach room temperature and stirred for further 4 h. The mixture was diluted with 100 ml dichloromethane and washed sequentially with a 5% KHSO$_4$-solution, water and brine. The organic phase was dried over anhydrous MgSO$_4$ and concentrated under reduced pressure to give methanesulfonic acid 2-tert-butoxycarbonylamino-1-methyl-ethyl ester in crude form as yellow oil.

Yield: 12.3 g MS (ES$^+$): m/e=254.

ii) Thioacetic acid S-(2-tert-butoxycarbonylamino-1-methyl-ethyl) ester

A solution of 11.9 g (47.0 mmol) crude methanesulfonic acid 2-tert-butoxycarbonylamino-1-methyl-ethyl ester in 100 ml DMF was added to a mixture of 5.0 g (1.4 equiv.) thioacetic acid and 15.3 g (1.0 equiv.) Cs$_2$CO$_3$ in 150 ml DMF. The reaction mixture was stirred for 4 h at 80° C. under argon and light protection. The mixture was poured into 300 ml water and extracted twice with 300 ml ethyl acetate each. The combined organic layers were washed with brine, dried over anhydrous MgSO$_4$ and concentrated under reduced pressure. Purification by flash chromatography on silica gel (eluent: CH$_2$Cl$_2$) gave pure thioacetic acid S-(2-tert-butoxycarbonylamino-1-methyl-ethyl) ester as brown oil.

Yield: 5.3 g MS (ES$^+$): m/e=234.

iii) 1-Amino-propane-2-sulfonic acid 5.25 g (22.5 mmol) Thioacetic acid S-(2-tert-butoxycarbonylamino-1-methyl-ethyl) ester were dissolved in 20 ml acetic acid. Under light protection a solution of 19.3 ml H$_2$O$_2$ (35% in water) in 50 ml acetic acid was added dropwise. The resulting mixture was stirred at room temperature for 24 h. After the reaction had been completed, argon was bubbled through the solution and 112 mg palladium on charcoal (10%) were added. After 90 minutes stirring at room temperature the mixture was filtered over "Celite". The filtrate was concentrated under reduced pressure and co-distilled three times with 150 ml toluene to give crude 1-amino-propane-2-sulfonic acid as a yellow oil. (The Boc-group was cleaved during the reaction.)

Yield: 3.48 g MS (ES$^+$): m/e=140.

iv) 1-Benzyloxycarbonylamino-propane-2-sulfonic acid

At 0° C. 1.16 ml (1.1 equiv.) benzyl chloroformate were added to a suspension of 1.0 g (7.19 mmol) 1-amino-propane- 2-sulfonic acid in 7.2 ml (1 equiv.) of an aqueous 1 M NaOH-solution. After 1 h the reaction mixture was allowed to warm to room temperature. After 24 h the reaction was not completed. Further 3.6 ml (0.5 equiv.) of an aqueous 1 M NaOH-solution and 0.5 ml (0.5 equiv.) benzyl chloroformate were added. After another 5 h stirring at room temperature the reaction mixture was filtered. The filter residue was taken up in ethyl acetate and purified by flash chromatography on silica gel (eluent: ethyl acetate/MeOH) to give pure 1-benzyloxy-carbonylamino-propane-2-sulfonic acid as a colorless oil.

Yield: 237 mg MS (ES$^+$): m/e=274.

v) (2-Chlorosulfonyl-propyl)-carbamic acid benzyl ester 230 mg (0.84 mmol) 1-Benzyloxy-carbonylamino-propane-2-sulfonic acid were suspended in 8 ml dichloromethane. 0.8 ml (1.8 equiv.) of a 20% phosgene solution in toluene and 0.1 ml DMF were added dropwise and the reaction mixture was stirred at room temperature. After 2 h the reaction mixture was concentrated under reduced pressure to give crude (2-chlorosulfonyl-propyl)-carbamic acid benzyl ester as yellow oil. Yield: 289 mg.

vi) [2-(1-Isopropyl-piperidin-4-ylsulfamoyl)-propyl]-carbamic acid benzyl ester 245 mg (0.84 mmol) of crude (2-chlorosulfonyl-propyl)-carbamic acid benzyl ester in 3 ml dichloromethane were added dropwise to a solution of 143 mg (1.2 equiv.) 1-isopropyl-piperidin-4-ylamine and 214 µl DIPEA in 3 ml dichloromethane. After 2 h stirring at room temperature the reaction mixture was washed with 5 ml of a saturated NaHCO$_3$-solution. The organic phase was dried over anhydrous MgSO$_4$ and concentrated under reduced pressure to give crude [2-(1-isopropyl-piperidin-4-ylsulfamoyl)-propyl]-carbamic acid benzyl ester as yellow oil.

Yield: 258 mg MS (ES$^+$): m/e=398.

vii) 1-Amino-propane-2-sulfonic acid (1-isopropyl-piperidin-4-yl)-amide 255 mg (0.64 mmol) crude [2-(1-isopropyl-piperidin-4-ylsulfamoyl)-propyl]-carbamic acid benzyl ester were dissolved in 10 ml MeOH. The solution was evacuated and rinsed with argon several times. 30 mg palladium on charcoal (10%) were added and again the mixture was evacuated and rinsed with argon several times. Finally argon was exchanged by hydrogen (balloon filled with hydrogen) and the mixture was stirred for 4 h at room temperature. The reaction mixture was filtered over "Celite" and the filter residue was washed with 10 ml MeOH. The filtrate was concentrated under vacuo to give crude 1-amino-propane-2-sulfonic acid (1-isopropyl-piperidin-4-yl)-amide as a colorless oil.

Yield: 106 mg MS (ES$^+$): m/e=264.

viii) 5-Chloro-thiophene-2-carboxylic acid [2-(1-isopropyl-piperidin-4-ylsulfamoyl)-propyl]-amide To a solution of 79 mg (1.2 equiv.) 5-chloro-thiophene-2-carboxylic acid in 3 ml DMF were added 184 mg (1.2 equiv.) HATU and 205 µl (3 equiv.) DIPEA. The resulting mixture was stirred for 30 min at room temperature. Subsequently a solution of 106 mg (0.40 mmol) crude 1-amino-propane-2-sulfonic acid (1-isopropyl-piperidin-4-yl)-amide and 68 µl (1 equiv.) DIPEA in 2 ml DMF was added. The resulting mixture was stirred for 4 h at room temperature and then concentrated under vacuo. The resulting residue was taken up in 10 ml dichloromethane and washed with a saturated NaHCO$_3$-solution and with brine. The organic phase was dried over anhydrous MgSO$_4$ and concentrated under reduced pressure. Final purification was achieved by preparative RP-HPLC (CH$_3$CN/H$_2$O gradient+0.1% TFA). The racemic product was obtained as trifluoroacetate. Subsequent transformation to the corresponding acetate gave a white amorphous solid.

Yield: 46 mg MS (ES$^+$): m/e=408, chloro pattern.

Example 27

5-Chloro-thiophene-2-carboxylic acid [(S)-1-hydroxymethyl-2-(1-isopropyl-piperidin-4-ylsulfamoyl)-ethyl]-amide i) (S)-3-Benzyloxy-2-benzyloxycarbonylamino-propane-1-sulfonic acid (S)-3-Benzyloxy-2-benzyloxycarbonylamino-propane-1-sulfonic acid was prepared by an analogous procedure as described in example 26 iv) starting from 1.76 g (7.19 mmol) (S)-2-amino-3-benzyloxy-propane-1-sulfonic acid and 1.16 ml (1.1 equiv.) benzyl chloroformate. Final purification by preparative RP-HPLC CH$_3$CN/H$_2$O gradient+0.1% TFA) gave pure (S)-3-benzyloxy-2-benzyloxycarbonylamino-propane-1-sulfonic acid as a colorless oil.

Yield: 380 mg MS (ES$^+$): m/e=380.

ii) (S)-1-Benzyloxymethyl-2-chlorosulfonyl-ethyl)-carbamic acid benzyl ester ((S)-1-Benzyloxymethyl-2-chlorosulfonyl-ethyl)-carbamic acid benzyl ester was prepared by an analogous procedure as described in example 26v) starting from 380 mg (1.0 mmol) (S)-3-benzyloxy-2-benzyloxycarbonylamino-propane-1-sulfonic acid. ((S)-1-Benzyloxymethyl-2-chlorosulfonyl-ethyl)-carbamic acid benzyl ester was obtained in crude form as colorless oil. Yield: 398 mg.

iii) [(S)-1-Benzyloxymethyl-2-(1-isopropyl-piperidin-4-ylsulfamoyl)-ethyl]-carbamic acid benzyl ester

[(S)-1-Benzyloxymethyl-2-(1-isopropyl-piperidin-4-ylsulfamoyl)-ethyl]-carbamic acid benzyl ester was prepared by an analogous procedure as described for example 26 vi) starting from 142 mg (1.0 equiv.) 1-isopropyl-piperidin-4-ylamine and 398 mg (1.0 mmol) ((S)-1-benzyloxymethyl-2-chlorosulfonyl-ethyl)-carbamic acid benzyl ester. The product was obtained in crude form as a light yellow foam. Yield: 217 mg MS (ES$^+$): m/e=504.

iv) (S)-2-Amino-3-hydroxy-propane-1-sulfonic acid (1-isopropyl-piperidin-4-yl)-amide 80 mg (0.16 mmol) [(S)-1-Benzyloxymethyl-2-(1-isopropyl-piperidin-4-ylsulfamoyl)-ethyl]-carbamic acid benzyl ester were dissolved in 3 ml dichloromethane. At 0° C., 0.32 ml of a 1 M BBr$_3$-solution in dichloromethane were added and the reaction mixture was allowed to warm to room temperature. After 24 h a few drops of water and 0.94 ml of a 1 M aqueous NaOH-solution were added. The mixture was concentrated under reduced pressure. The residue was taken up in DMF and filtered in order to get rid of salts. The filtrate was concentrated under vacuo to give crude (S)-2-amino-3-hydroxy-propane-1-sulfonic acid (1-isopropyl-piperidin-4-yl)-amide, which was pure enough for further transformations. Yield:

65 mg MS (ES$^+$): m/e=280.

v) 5-Chloro-thiophene-2-carboxylic acid [(S)-1-hydroxymethyl-2-(1-isopropyl-piperidin-4-ylsulfamoyl)-ethyl]-amide 5-Chloro-thiophene-2-carboxylic acid [(S)-1-hydroxymethyl-2-(1-isopropyl-piperidin-4-ylsulfamoyl)-ethyl]-amide was prepared by an analogous procedure as described in example 26 viii) starting from 28 mg (1.1 equiv.) 5-chloro-thiophene-2-carboxylic acid and 44 mg (0.16 mmol) (S)-2-amino-3-hydroxy-propane-1-sulfonic acid (1-isopropyl-piperidin-4-yl)-amide. Final purification by preparative RP-HPLC (CH$_3$CN/H$_2$O gradient+0.1% TFA) gave pure 5-chloro-thiophene-2-carboxylic acid [(S)-1-hydroxymethyl-2-(1-isopropyl-piperidin-4-ylsulfamoyl)-ethyl]-amide. The title compound was obtained as its trifluoroacetate in form of a colorless amorphous material.

Yield: 15 mg MS (ES$^+$): m/e=424, chloro pattern.

Example 28

5-Chloro-thiophene-2-carboxylic acid [2-(1-isopropyl-piperidin-4-ylsulfamoyl)-1,1-dimethyl-ethyl]-amide i) Methanesulfonic acid 2-(9H-fluoren-9-ylmethoxycarbonylamino)-2-methyl-propyl ester Methanesulfonic acid 2-(9H-fluoren-9-ylmethoxycarbonylamino)-2-methyl-propyl ester was prepared by an analogous procedure as described in example 26i) starting from 4.95 g (15.9 mmol) (2-hydroxy-1,1-dimethyl-ethyl)-carbamic acid 9H-fluoren-9-ylmethyl ester and 1.5 ml (1.2 equiv.) methanesulfonyl chloride. Methanesulfonic acid 2-(9H-fluoren-ylmethoxycarbonylamino)-2-methyl-propyl ester was obtained in crude form as yellow oil. Yield: 7.0 g.

ii) Thioacetic acid S-[2-(9H-fluoren-9-ylmethoxycarbonylamino)-2-methyl-propyl]ester Thioacetic acid S-[2-(9H-fluoren-9-ylmethoxycarbonylamino)-2-methyl-propyl]ester was prepared by an analogous procedure as described in example 26 ii) starting from 6.19 g (15.9 mmol) methanesulfonic acid 2-(9H-fluoren-9-ylmethoxycarbonylamino)-2-methyl-propyl ester and 2.1 ml (1.8 equiv.) thioacetic acid. Purification by flash chromatography on silica gel (eluent: CH$_2$Cl$_2$) gave pure thioacetic acid S-[2-(9H-fluoren-9-ylmethoxycarbonylamino)-2-methyl-propyl]ester as yellow oil. Yield: 1.87 g MS (ES$^+$): m/e=370.

iii) 2-(9H-Fluoren-9-ylmethoxycarbonylamino)-2-methyl-propane-1-sulfonic acid 2-(9H-Fluoren-9-ylmethoxycarbonylamino)-2-methyl-propane-1-sulfonic acid was prepared by an analogous procedure as described in example 26 iii) starting from 1.87 g (5.1 mmol) thioacetic acid S-[2-(9H-fluoren-9-ylmethoxycarbonylamino)-2-methyl-propyl]ester and 4.3 ml H$_2$O$_2$ (35% in water) in 20 ml acetic acid. Purification by flash chromatography on silica gel (eluent: ethyl acetate/methanol) gave pure 2-(9H-fluoren-9-ylmethoxycarbonylamino)-2-methyl-propane-1-sulfonic acid as yellow oil. Yield: 771 mg MS (ES$^+$): m/e=376.

iv) (2-Chlorosulfonyl-1,1-dimethyl-ethyl)-carbamic acid 9H-fluoren-9-ylmethyl ester (2-Chlorosulfonyl-1,1-dimethyl-ethyl)-carbamic acid 9H-fluoren-9-ylmethyl ester was prepared by an analogous procedure as described in example 26v) starting from 457 mg (1.2 mmol) 2-(9H-fluoren-9-ylmethoxycarbonylamino)-2-methyl-propane-1-sulfonic acid and 2.3 ml (3.6 equiv.) phosgene (20% in toluene). (2-Chlorosulfonyl-1,1-dimethyl-ethyl)-carbamic acid 9H-fluoren-9-ylmethyl ester was obtained in crude form as a colorless oil. Yield: 503 mg v) [2-(1-Isopropyl-piperidin-4-ylsulfamoyl)-1,1-dimethyl-ethyl]-carbamic acid 9H-fluoren-9-ylmethyl ester

[2-(1-Isopropyl-piperidin-4-ylsulfamoyl)-1,1-dimethyl-ethyl]-carbamic acid 9H-fluoren-9-ylmethyl ester was prepared by an analogous procedure as described in example 26 vi) starting from 479 mg (1.2 mmol) (2-chlorosulfonyl-1,1-dimethyl-ethyl)-carbamic acid 9H-fluoren-9-ylmethyl ester and 208 mg (1.2 equiv.) 1-isopropyl-piperidin-4-ylamine. The product was obtained in crude form as light yellow foam. Yield: 678 mg MS (ES$^+$): m/e=500.

vi) 2-Amino-2-methyl-propane-1-sulfonicacid (1-isopropyl-piperidin-4-yl)-amide 607 mg (1.2 mmol) of crude [2-(1-isopropyl-piperidin-4-ylsulfamoyl)-1,1-dimethyl-ethyl]-carbamic acid 9H-fluoren-9-ylmethyl ester were dissolved in 6 ml DMF. 1.5 ml morpholine were added and the resulting mixture was stirred for 2 h at room temperature. The reaction mixture was filtered. The filtrate was concentrated under reduced pressure and co-distilled three times with 20 ml DMF to give crude 2-amino-2-methyl-propane-1-sulfonicacid (1-isopropyl-piperidin-4-yl)-amide as yellow oil. Yield: 360 mg MS (ES$^+$): m/e=278.

vii) 5-Chloro-thiophene-2-carboxylic acid [2-(1-isopropyl-piperidin-4-ylsulfamoyl)-1,1-dimethyl-ethyl]-amide 5-Chloro-thiophene-2-carboxylic acid [2-(1-isopropyl-piperidin-4-ylsulfamoyl)-1,1-dimethyl-ethyl]-amide was prepared by an analogous procedure as described in example 26 viii) starting from 195 mg (1 equiv.) 5-chloro-thiophene-2-carboxylic acid and 332 mg (1.2 mmol) 2-amino-2-methyl-propane-1-sulfonicacid (1-isopropyl-piperidin-4-yl)-amide. Final purification by preparative RP-HPLC (CH$_3$CN/H$_2$O gradient+0.1% TFA) gave pure 5-chloro-thiophene-2-carboxylic acid [2-(1-isopropyl-piperidin-4-ylsulfamoyl)-1,1-dimethyl-ethyl]-amide. The title compound was obtained as its trifluoroacetate in form of a colorless amorphous material.

Yield: 173 mg MS (ES$^+$): m/e=422, chloro pattern.

Example 29

5-Chloro-thiophene-2-carboxylic acid [3-(1-isopropyl-piperidin-4-ylsulfamoyl)-propyl]-amide i) 3-Chloro-propane-1-sulfonic acid (1-isopropyl-piperidin-4-yl)-amide 2.00 g (11.29 mmol) 3-Chloro-propane-1-sulfonyl chloride were dissolved in 20 ml dichloromethane. At 0° C. a solution of 1.6 g (1 equiv.) 1-isopropyl-piperidin-4-ylamine in 10 ml dichloromethane was added slowly via a syringe. The reaction mixture was stirred for 3 h at 0° C. The formed precipitate was filtered off and washed once with 10 ml cold dichloromethane and twice with 10 ml diethyl ether. The product was obtained as its hydrochloride in form of a light brown crystalline material. Yield: 2.7 g MS (ES$^+$): m/e=283.

ii) 3-Azido-propane-1-sulfonic acid (1-isopropyl-piperidin-4-yl)-amide 183 mg (3 equiv.) NaN$_3$ were added to a mixture of 300 mg (0.94 mmol) 3-chloro-propane-1-sulfonic acid (1-isopropyl-piperidin-4-yl)-amide hydrochloride and 519 mg K$_2$CO$_3$ in 10 ml DMF. The resulting mixture was stirred for 24 h at 50° C. The reaction mixture was concentrated under reduced pressure. The resulting residue was taken up in dichloromethane and filtered. The filtrate was concentrated under vacuo to give crude 3-azido-propane-1-sulfonic acid (1-isopropyl-piperidin-4-yl)-amide as a yellow oil, which was pure enough for further transformations.
Yield: 250 mg iii) 3-Amino-propane-1-sulfonic acid (1-isopropyl-piperidin-4-yl)-amide 250 mg (0.86 mmol) crude 3-azido-propane-1-sulfonic acid (1-isopropyl-piperidin-4-yl)-amide were dissolved in 10 ml MeOH. The solution was evacuated and rinsed with argon several times. 30 mg palladium on charcoal (10%) were added and again the mixture was evacuated and rinsed with argon several times. Finally argon was exchanged by hydrogen (balloon filled with hydrogen) and the mixture was stirred for 4 h at room temperature. The reaction mixture was filtered over "Celite" and the filter residue was washed with 10 ml MeOH. The filtrate was concentrated under vacuo to give crude 3-amino-propane-1-sulfonic acid (1-isopropyl-piperidin-4-yl)-amide as yellow oil. Yield: 200 mg MS (ES$^+$): m/e=264.

iv) 5-Chloro-thiophene-2-carboxylic acid [3-(1-isopropyl-piperidin-4-ylsulfamoyl)-propyl]-amide 5-Chloro-thiophene-2-carboxylic acid [3-(1-isopropyl-piperidin-4-ylsulfamoyl)-propyl]-amide was prepared by an analogous procedure as described in example 5 iii) starting from 120 mg (1 equiv.) 5-chloro-thiophene-2-carboxylic acid and 195 mg (0.74 mmol) 3-amino-propane-1-sulfonic acid (1-isopropyl-piperidin-4-yl)-amide. Final purification by preparative RP-HPLC (CH$_3$CN/H$_2$O gradient+0.1% TFA) gave pure 5-chloro-thiophene-2-carboxylic acid [3-(1-isopropyl-piperidin-4-ylsulfamoyl)-propyl]-amide. The title compound was obtained as its trifluoroacetate in form of a colorless amorphous material.
Yield: 200 mg MS (ES$^+$): m/e=408, chloro pattern.

Example 30

4-[(5-Chloro-thiophene-2-carbonyl)-amino]-3-(1-isopropyl-piperidin-4-ylsulfamoyl)-butyric acid i) 4-Benzyloxycarbonylamino-3-hydroxy-butyric acid benzyl ester To a mixture of 5.0 g (19.7 mmol) 4-benzyloxycarbonylamino-3-hydroxy-butyric acid and 6.36 g (1 equiv.) tetra-n-butyl ammonium bromide in 70 ml dichloromethane and 50 ml of an aqueous saturated NaHCO$_3$-solution were added 2.35 ml (1 equiv.) benzyl bromide. The resulting mixture was stirred vigorously for 72 h at room temperature. The organic layer was separated, washed three times with brine, dried over anhydrous MgSO$_4$ and concentrated under reduced pressure. Purification by flash chromatography on silica gel (eluent: heptane/ethyl acetate) gave pure 4-benzyloxycarbonylamino-3-hydroxy-butyric acid benzyl ester as colorless oil.
Yield: 6.7 g MS (ES$^+$): m/e=344.

ii) 4-Benzyloxycarbonylamino-3-methanesulfonyloxy-butyric acid benzyl ester

4-Benzyloxycarbonylamino-3-methanesulfonyloxy-butyric acid benzyl ester was prepared by an analogous procedure as described in example 26i) starting from 6.7 g (19.6 mmol) 4-benzyloxycarbonylamino-3-hydroxy-butyric acid benzyl ester and 1.84 ml (1.2 equiv.) methanesulfonyl chloride. 4-Benzyloxycarbonylamino-3-methanesulfonyloxy-butyric acid benzyl ester was obtained in crude form as yellow oil. Yield: 8.5 g.

iii) 3-Acetylsulfanyl-4-benzyloxycarbonylamino-butyric acid benzyl ester

To a solution of 250 mg (0.59 mmol) 4-benzyloxycarbonylamino-3-methanesulfonyloxy-butyric acid benzyl ester in 5 ml DMF were added sequentially 68 mg (1.0 equiv.) potassium thioacetate and 101 µl (1.0 equiv.) DIPEA. The reaction mixture was stirred for 2 h at 80° C. under argon and light protection. Further 68 mg (1.0 equiv.) potassium thioacetate and 101 µl (1.0 equiv.) DIPEA were added. After stirring for another 2 h at 80° C., the mixture was poured into 10 ml water and extracted three times with 15 ml ethyl acetate. The combined organic layers were washed with brine, dried over anhydrous MgSO$_4$ and concentrated under reduced pressure. Purification by flash chromatography on silica gel (eluent: heptane/ethyl acetate) gave pure 3-acetylsulfanyl-4-benzyloxycarbonylamino-butyric acid benzyl ester as yellow oil.
Yield: 180 mg MS (ES$^+$): m/e=402.

iv) 4-Benzyloxycarbonylamino-3-sulfo-butyric acid benzyl ester

4-Benzyloxycarbonylamino-3-sulfo-butyric acid benzyl ester was prepared by an analogous procedure as described in example 26 iii) starting from 180 mg (0.45 mmol) 3-acetyl-sulfanyl-4-benzyloxycarbonylamino-butyric acid benzyl ester and 0.4 ml H$_2$O$_2$ (35% in water) in 5 ml acetic acid. The product was obtained in crude form as colorless oil.
Yield: 163 mg MS (ES$^+$): m/e=408.

v) 4-Benzyloxycarbonylamino-3-chlorosulfonyl-butyric acid benzyl ester 163 mg (0.40 mmol) crude 4-benzyloxycarbonylamino-3-sulfo-butyric acid benzyl ester as obtained in iv) were co-distilled three times with 10 ml toluene. The resulting residue was dissolved in 5 ml dichloromethane. 0.4 ml (1.8 equiv.) of a 20% phosgene solution in toluene and 0.1 ml DMF were added and the reaction mixture was stirred at room temperature. After 20 h the reaction mixture was concentrated under reduced pressure to give crude 4-benzyl-oxycarbonylamino-3-chlorosulfonyl-butyric acid benzyl ester as yellow oil, which was used without further purification for the next reaction. Yield: 170 mg.

vi) 4-Benzyloxycarbonylamino-3-(1-isopropyl-piperidin-4-ylsulfamoyl)-butyric acid benzyl ester 4-Benzyloxycarbonylamino-3-(1-isopropyl-piperidin-4-ylsulfamoyl)-butyric acid benzyl ester was prepared by an analogous procedure as described in example 26 vi) starting from 170 mg (0.40 mmol) 4-benzyl-oxycarbonylamino-3-chlorosulfonyl-butyric acid benzyl ester and 57 mg (1.0 equiv.) 1-isopropyl-piperidin-4-ylamine. Final purification by preparative RP-HPLC (CH$_3$CN/H$_2$O gradient+0.1% TFA) gave pure 4-benzyloxycarbonylamino-3-(1-isopropyl-piperidin-4-ylsulfamoyl)-butyric acid benzyl ester. The title compound was obtained as its trifluoroacetate in form of a brown amorphous material.
Yield: 26 mg MS (ES$^+$): m/e=532.

vii) 4-Amino-3-(1-isopropyl-piperidin-4-ylsulfamoyl)-butyric acid 24 mg (0.04 mmol) 4-Benzyloxycarbonylamino-3-(1-isopropyl-piperidin-4-ylsulfamoyl)-butyric acid benzyl ester were dissolved in 3 ml dichloromethane. At 0° C., 0.1 ml of a 1 M BBr$_3$-solution in dichloromethane were added and the reaction mixture was allowed to warm to room temperature. After 24 h a few drops of water and 0.3 ml of a 1 M aqueous NaOH-solution were added. The mixture was concentrated under reduced pressure. The residue was taken up in DMF and filtered in order to get rid of salts. The filtrate was concentrated under vacuo to give crude 4-amino-3-(1-isopropyl-piperidin-4-ylsulfamoyl)-butyric acid, which was pure enough for further transformations. Yield: 14 mg
MS (ES$^+$): m/e=308.

viii) 4-[(5-Chloro-thiophene-2-carbonyl)-amino]-3-(1-isopropyl-piperidin-4-ylsulfamoyl)-butyric acid To a solution of 10 mg (1.4 equiv.) 5-chloro-thiophene-2-carboxylic acid in 2 ml DMF were added 24 mg (1.4 equiv.) HATU and 23 µl (3 equiv.) DIPEA. The resulting mixture was stirred for 15 min at room temperature. Subsequently a solution of 14 mg (0.04 mmol) crude 4-amino-3-(1-isopropyl-piperidin-4-ylsulfamoyl)-butyric acid in 2 ml DMF was added. The resulting mixture was stirred for 45 min at room temperature. After that time a few drops of water were added and the mixture was purified by preparative RP-HPLC (CH$_3$CN/H$_2$O gradient+0.1% TFA). The racemic product was obtained as trifluoroacetate.
Yield: 5 mg MS (ES$^+$): m/e=452, chloro pattern.

Example 31

5-Chloro-thiophene-2-carboxylic acid [2-(1-isopropyl-piperidin-4-yl)-1,1,3-trioxo-1λ$^6$-isothiazolidin-5-ylmethyl]-amide

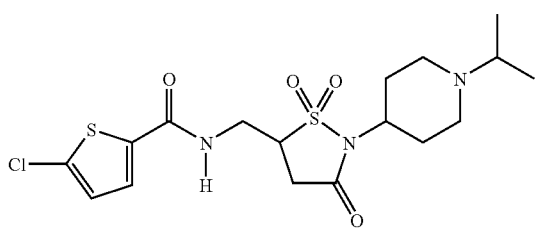

To a solution of 10 mg (1.4 equiv.) 5-chloro-thiophene-2-carboxylic acid in 2 ml DMF were added 24 mg (1.4 equiv.) HATU and 23 µl (3 equiv.) DIPEA. The resulting mixture was stirred for 15 min at room temperature. Subsequently a solution of 14 mg (0.04 mmol) crude 4-amino-3-(1-isopropyl-piperidin-4-ylsulfamoyl)-butyric acid in 2 ml DMF was added. The resulting mixture was stirred for 5 h at room temperature. The reaction mixture was concentrated under reduced pressure and purified by preparative RP-HPLC (CH$_3$CN/H$_2$O gradient+0.1% TFA). The racemic product was obtained as trifluoroacetate. Yield: 9 mg
MS (ES$^+$): m/e=434, chloro pattern.

Example 32

5-Chloro-thiophene-2-carboxylic acid {2-[[5-(5-chloro-thiophen-2-yl)-isoxazol-3-ylmethyl]-(1-isopropyl-piperidin-4-yl)-sulfamoyl]-ethyl}-amide 5-Chloro-thiophene-2-carboxylic acid {2-[[5-(5-chloro-thiophen-2-yl)-isoxazol-3-ylmethyl]-(1-isopropyl-piperidin-4-yl)-sulfamoyl]-ethyl}-amide was prepared by an analogous procedure as described in example 15 starting from 141 mg (2 equiv.) 3-bromomethyl-5-(5-chloro-thiophen-2-yl)-isoxazole and 100 mg (0.25 mmol) 5-chloro-thiophene-2-carboxylic acid [2-(1-isopropyl-piperidin-4-ylsulfamoyl)-ethyl]-amide. Final purification by preparative RP-HPLC (CH$_3$CN/H$_2$O gradient+0.1% TFA) gave pure 5-Chloro-thiophene-2-carboxylic acid {2-[[5-(5-chloro-thiophen-2-yl)-isoxazol-3-ylmethyl]-(1-isopropyl-piperidin-4-yl)-sulfamoyl]-ethyl}-amide. The title compound was obtained as its trifluoroacetate in form of a colorless amorphous material.
Yield: 67 mg MS (ES$^+$): m/e=591, chloro pattern.

Example 33

5-Chloro-thiophene-2-carboxylic acid {2-[(5-cyclopropyl-[1,3,4]thiadiazol-2-ylmethyl)-(1-isopropyl-piperidin-4-yl)-sulfamoyl]-ethyl}-amide 5-Chloro-thiophene-2-carboxylic acid {2-[(5-cyclopropyl-[1,3,4]thiadiazol-2-ylmethyl)-(1-isopropyl-piperidin-4-yl)-sulfamoyl]-ethyl}-amide was prepared by an analogous procedure as described in example 15 starting from 89 mg (2 equiv.) 2-chloromethyl-5-cyclopropyl-[1,3,4]thiadiazole and 100 mg (0.25 mmol) 5-chloro-thiophene-2-carboxylic acid [2-(1-isopropyl-piperidin-4-ylsulfamoyl)-ethyl]-amide. Final purification by preparative RP-HPLC (CH$_3$CN/H$_2$O gradient+0.1% TFA) gave pure 5-chloro-thiophene-2-carboxylic acid {2-[(5-cyclopropyl-[1,3,4]thiadiazol-2-ylmethyl)-(1-isopropyl-piperidin-4-yl)-sulfamoyl]-ethyl}-amide. The title compound was obtained as its trifluoroacetate in form of a colorless amorphous material.
Yield: 42 mg MS (ES$^+$): m/e=532, chloro pattern.

Example 34

5-Chloro-thiophene-2-carboxylic acid {2-[[(5-chloro-pyridin-2-ylcarbamoyl)-methyl]-(1-isopropyl-piperidin-4-yl)-sulfamoyl]-ethyl}-amide 5-Chloro-thiophene-2-carboxylic acid {2-[[(5-chloro-pyridin-2-ylcarbamoyl)-methyl]-(1-isopropyl-piperidin-4-yl)-sulfamoyl]-ethyl}-amide was prepared by an analogous procedure as described in example 15 starting from 168 mg (2 equiv.) 2-bromo-N-(5-chloro-pyridin-2-yl)-acetamide and 133 mg (0.34 mmol) 5-chloro-thiophene-2-carboxylic acid [2-(1-isopropyl-piperidin-4-ylsulfamoyl)-ethyl]-amide.

Final purification by preparative RP-HPLC (CH₃CN/H₂O gradient+0.1% TFA) gave pure 5-chloro-thiophene-2-carboxylic acid {2-[[(5-chloro-pyridin-2-ylcarbamoyl)-methyl]-(1-isopropyl-piperidin-4-yl)-sulfamoyl]-ethyl}-amide. The title compound was obtained as its trifluoroacetate in form of a colorless amorphous material.

Yield: 28 mg MS (ES⁺): m/e=562, chloro pattern.

According to the previous examples the following compounds can be prepared accordingly:

5-Chloro-thiophene-2-carboxylic acid [3-hydroxy-2-(1-isopropyl-piperidin-4-ylsulfamoyl)-propyl]-amide,
5-Chloro-thiophene-2-carboxylic acid [2-(1-isopropyl-piperidin-4-ylsulfamoyl)-3-methoxy-propyl]-amide,
5-Chloro-thiophene-2-carboxylic acid [4-hydroxy-2-(1-isopropyl-piperidin-4-ylsulfamoyl)-butyl]-amide,
5-Chloro-thiophene-2-carboxylic acid [2-(1-isopropyl-piperidin-4-ylsulfamoyl)-4-methoxy-butyl]-amide,
5-Chloro-thiophene-2-carboxylic acid [3-carbamoyl-2-(1-isopropyl-piperidin-4-ylsulfamoyl)-propyl]-amide,
5-Chloro-thiophene-2-carboxylic acid [3-dimethylcarbamoyl-2-(1-isopropyl-piperidin-4-ylsulfamoyl)-propyl]-amide,
5-Chloro-thiophene-2-carboxylic acid [2-(1-isopropyl-piperidin-4-ylsulfamoyl)-4-morpholin-4-yl-4-oxo-butyl]-amide,
5-Chloro-thiophene-2-carboxylic acid [2-(1-isopropyl-piperidin-4-ylsulfamoyl)-4-(4-methyl-piperazin-1-yl)-4-oxo-butyl]-amide,
5-Chloro-thiophene-2-carboxylic acid (2-{(1-isopropyl-piperidin-4-yl)-[2-(4-methyl-piperazin-1-yl)-2-oxo-ethyl]-sulfamoyl}-ethyl)-amide,
5-Chloro-thiophene-2-carboxylic acid {2-[benzenesulfonylmethyl-(1-isopropyl-piperidin-4-yl)-sulfamoyl]-ethyl}-amide,
5-Chloro-thiophene-2-carboxylic acid {2-[(3-amino-benzo[d]isoxazol-5-ylmethyl)-(1-isopropyl-piperidin-4-yl)-sulfamoyl]-ethyl}-amide,
5-Chloro-thiophene-2-carboxylic acid {2-[(1-isopropyl-piperidin-4-yl)-(5-methyl-isoxazol-3-yl)-sulfamoyl]-ethyl}-amide,
5-Chloro-thiophene-2-carboxylic acid {2-[(1-isopropyl-piperidin-4-yl)-(5-methyl-thiazol-2-yl)-sulfamoyl]-ethyl}-amide,
5-Chloro-thiophene-2-carboxylic acid {2-[(1-isopropyl-piperidin-4-yl)-pyridin-2-yl-sulfamoyl]-ethyl}-amide,
5-Chloro-thiophene-2-carboxylic acid {2-[cyclopropanecarbonyl-(1-isopropyl-piperidin-4-yl)-sulfamoyl]-ethyl}-amide,
5-Chloro-thiophene-2-carboxylic acid [2-(1-isopropyl-piperidin-4-yl)-1,1-dioxo-1$\lambda^6$-isothiazolidin-5-ylmethyl]-amide,

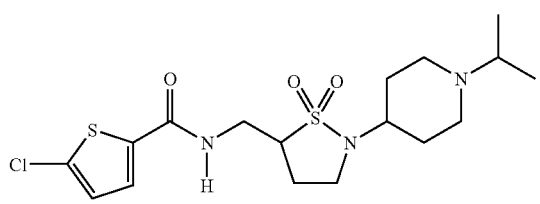

5-Chloro-thiophene-2-carboxylic acid [2-(1-isopropyl-piperidin-4-yl)-1,1-dioxo-1$\lambda^6$-[1,2]thiazinan-6-ylmethyl]-amide,

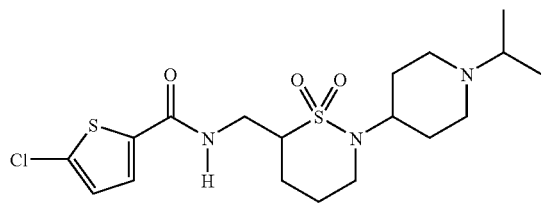

5-Chloro-thiophene-2-carboxylic acid [2-(1-isopropyl-piperidin-4-yl)-1,1,3-trioxo-1$\lambda^6$-[1,2]thiazinan-6-ylmethyl]-amide,

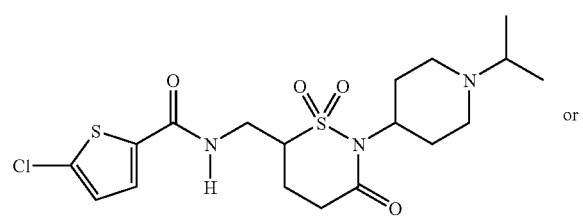

or

5-Chloro-thiophene-2-carboxylic acid [3-(1-isopropyl-piperidin-4-yl)-2,4,4-trioxo-4$\lambda^6$-[1,4,3]oxathiazinan-5-ylmethyl]-amide.

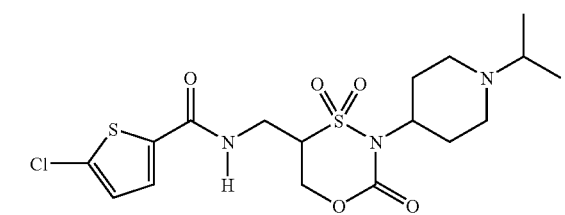

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i.e. the IC₅₀ value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula I. For calculating the inhibition constant Ki, the IC₅₀ value was corrected for competition with substrate using the formula $Ki = IC_{50}/\{1+(\text{substrate concentration}/Km)\}$ wherein Km is the Michaelis-Menten constant (Chen and Prusoff, Biochem. Pharmacol. 22 (1973) 3099-3108; I. H. Segal, Enzyme Kinetics, 1975, John Wiley & Sons, New York, 100-125).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN₃) was used. The IC₅₀ was determined by combining in appropriate wells of a Costar half-area microtiter plate 25 μl human factor Xa (Enzyme Research Laboratories, Inc.; South Bend, Ind.) in TBS-PEG; 40 μl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I or Ia plus enzyme for 10 min. Then the assay was initiated by adding substrate to obtain a final volume of 100 μl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 μM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059). Kinetic assays were conducted at 25° C. in half-area microtiter plates (Costar Corp., Cambridge, Mass.) using a kinetic plate reader (Molecular Devices Spectramax 250). A typical assay consisted of 25 μl human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM $CaCl_2$, 0.05% PEG 8000, pH 8.15). Following a 15 minutes preincubation period, the assay was initiated by the addition of 35 μl of the chromogenic substrate S-2288 (D-Ile-Pro-Arg-p-nitroanilide, Pharmacia Hepar Inc., 500 μM final concentration).

The results (inhibition constants Ki FXa in mikro M [μM]) for inhibition of factor Xa are shown in Table 1.

TABLE 1

| Example | Ki (FXa) [μM] |
|---|---|
| 1 | 0.010 |
| 2 | 0.167 |
| 3 | 0.007 |
| 4 | 0.015 |
| 5 | 0.066 |
| 6 | 20.477 |
| 7 | 7.254 |
| 8 | 1.103 |
| 9 | 0.006 |
| 10 | 0.259 |
| 11 | 3.153 |
| 12 | 0.572 |
| 13 | 4.467 |
| 14 | 19.592 |
| 15 | 0.005 |
| 16 | 0.004 |
| 17 | 0.004 |
| 18 | 0.005 |
| 19 | 0.005 |
| 20 | 0.003 |
| 21 | 0.004 |
| 22 | 0.008 |
| 23 | 0.006 |
| 24 | 0.004 |
| 25 | 0.003 |
| 26 | 0.013 |
| 27 | 1.254 |
| 28 | 3.387 |
| 29 | 0.399 |
| 31 | 0.032 |
| 32 | 0.006 |
| 33 | 0.006 |

What is claimed is:

1. A compound of formula Ia:

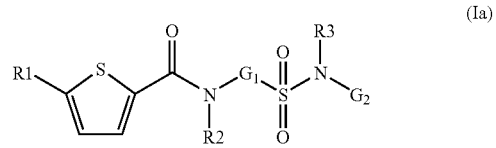

wherein:
R1 is bromine, methyl or chlorine,
R2 is hydrogen atom,
R3 is a hydrogen atom, —($C_0$-$C_1$)-alkylene-C(O)—NH—R6, —($C_0$-$C_1$)-alkylene-C(O)—N(R21)-R22, —($C_0$-$C_2$)-alkylene-C(O)—R10, —($C_0$-$C_1$)-alkylene-($C_1$-$C_2$)-perfluoroalkyl, —($C_1$-$C_3$)-alkyl, —($C_1$-$C_2$)-alkylene-S(O)$_2$-phenyl, —($C_1$-$C_3$)-alkylene-O—R10 or —($C_0$-$C_4$)-alkylene-heterocyclyl, wherein heterocyclyl is as defined below and is unsubstituted or mono- or disubstituted independently of one another by R8,
R6 is heterocyclyl, wherein heterocyclyl is selected from benzisoxazolyl, isoxazolyl, morholinyl, pyridyl, thiazolyl, thiadiazolyl and thienyl, and wherein heterocyclyl is independently of one another unsubstituted or mono-, di- or trisubstituted by R7,
R7 is chlorine or =O,
R8 is —($C_3$-$C_6$)-cycloalkyl, —$NH_2$, —($C_1$-$C_4$)-alkyl, or heterocyclyl, wherein heterocyclyl is as defined above and independently of one another unsubstituted or mono- or disubstituted by R7,
R10 is hydrogen atom, —($C_0$-$C_2$)-alkylene-($C_3$-$C_6$)-cycloalkyl or —($C_1$-$C_4$)-alkyl,
R21 and R22 are independently of one another identical or different and are hydrogen atom or —($C_1$-$C_4$)-alkyl,
R21 and R22 together with the nitrogen atom to which they are bonded can form a heterocyclic ring from the group N-methyl-piperazine and morpholine,
$G_1$ is —($C_2$-$C_4$)-alkylene, wherein —($C_2$-$C_4$)-alkylene is unsubstituted or mono- or disubstituted independently of one another by R13,
R13 is a hydrogen atom, —($C_1$-$C_2$)-alkylene-O—R22, —($C_1$-$C_2$)-alkylene-OH, —($C_0$-$C_2$)-alkylene-C(O)—OH, —($C_0$-$C_1$)-alkylene-C(O)—N(R21)-R22, or —($C_1$-$C_4$)-alkyl, or
R13 and R3 together with the atoms to which they are bonded form a isothiazolidine 1,1-dioxide, [1,2]thiazinane 1,1-dioxide or [1,4,3]oxathiazinane 4,4-dioxide group and wherein said group is unsubstituted or substituted one time by =O,
$G_2$ is azetidine, piperazine or piperidine, wherein G2 is unsubstituted or monosubstituted by isopropyl, cyclopropyl, benzyl or pyridyl, and stereoisomeric forms and physiologically tolerable salts thereof.

2. A compound of formula Ia according to claim 1, wherein the compound of formula Ia is:
5-Chloro-thiophene-2-carboxylic acid [2-(1-isopropyl-piperidin-4-ylsulfamoyl)-ethyl]-amide,
5-Chloro-thiophene-2-carboxylic acid [2-(1-cyclopropyl-piperidin-4-ylsulfamoyl)-ethyl]-amide,
5-Chloro-thiophene-2-carboxylic acid {2-[(1-isopropyl-piperidin-4-yl)-methyl-sulfamoyl]-ethyl}-amide,
5-Chloro-thiophene-2-carboxylic acid {2-[(1-isopropyl-piperidin-4-yl)-(2,2,2-trifluoro-ethyl)-sulfamoyl]-ethyl}-amide,
5-Chloro-thiophene-2-carboxylic acid [2-(3,4,5,6-tetrahydro-2H-[1,4']bipyridinyl-4-ylsulfamoyl)-ethyl]-amide, 5-Chloro-thiophene-2-carboxylic acid[2-(azetidin-3-yl-sulfamoyl)-ethyl]amide,
5-Chloro-thiophene-2-carboxylic acid [2-(1-isopropyl-azetidin-3-ylsulfamoyl)-ethyl]-amide,
5-Chloro-thiophene-2-carboxylic acid [2-(4-benzyl-piperazin-1-ylsulfamoyl)-ethyl]-amide,
5-Bromo-thiophene-2-carboxylic acid[2-(1-isopropyl-piperidin-4-ylsulfamoyl)-ethyl]-amide,
5-Methyl-thiophene-2-carboxylic acid [2-(1-isopropyl-piperidin-4-ylsulfamoyl)-ethyl]-amide,
5-Chloro-thiophene-2-carboxylic acid {2-[(1-isopropyl-piperidin-4-yl)-(2-methoxy-ethyl)-sulfamoyl]-ethyl}-amide,
5-Chloro-thiophene-2-carboxylic acid {2-[(2-hydroxy-ethyl)-(1-isopropyl-piperidin-4-yl)-sulfamoyl]-ethyl}-amide,
5-Chloro-thiophene-2-carboxylic acid {2-[(3-hydroxy-propyl)-(1-isopropyl-piperidin-4-yl)-sulfamoyl]-ethyl}-amide,
5-Chloro-thiophene-2-carboxylic acid {2-[dimethylcarbamoylmethyl-(1-isopropyl-piperidin-4-yl)-sulfamoyl]-ethyl}-amide,
5-Chloro-thiophene-2-carboxylic acid {2-[(1-isopropyl-piperidin-4-yl)-(2-morpholin-4-yl-2-oxo-ethyl)-sulfamoyl]-ethyl}-amide,
5-Chloro-thiophene-2-carboxylic acid {2-[carbamoylmethyl-(1-isopropyl-piperidin-4-yl)-sulfamoyl]-ethyl}-amide,
5-Chloro-thiophene-2-carboxylic acid {2-[(1-isopropyl-piperidin-4-yl)-(5-methyl-isoxazol-3-ylmethyl)-sulfamoyl]-ethyl}-amide,
5-Chloro-thiophene-2-carboxylic acid {2-[(1-isopropyl-piperidin-4-yl)-pyridin-3-ylmethyl-sulfamoyl]-ethyl}-amide,
5-Chloro-thiophene-2-carboxylic acid {2-[(1-isopropyl-piperidin-4-yl)-thiazol-2-ylmethyl-sulfamoyl]-ethyl}-amide,
5-Chloro-thiophene-2-carboxylic acid {2-[(1-isopropyl-piperidin-4-yl)-propylaminocarbonyl-sulfamoyl]-ethyl}-amide,
5-Chloro-thiophene-2-carboxylic acid {2-[acetyl-(1-isopropyl-piperidin-4-yl)-sulfamoyl]-ethyl}-amide,
5-Chloro-thiophene-2-carboxylic acid [2-(1-isopropyl-piperidin-4-ylsulfamoyl)-propyl]-amide,
5-Chloro-thiophene-2-carboxylic acid [(S)-1-hydroxymethyl-2-(1-isopropyl-piperidin-4-ylsulfamoyl)-ethyl]-amide,
5-Chloro-thiophene-2-carboxylic acid [2-(1-isopropyl-piperidin-4-ylsulfamoyl)-1,1-dimethyl-ethyl]-amide,
5-Chloro-thiophene-2-carboxylic acid [3-(1-isopropyl-piperidin-4-ylsulfamoyl)-propyl]-amide,
4-[(5-Chloro-thiophene-2-carbonyl)-amino]-3-(1-isopropyl-piperidin-4-ylsulfamoyl)-butyric acid,
5-Chloro-thiophene-2-carboxylic acid [2-(1-isopropyl-piperidin-4-yl)-1,1,3-trioxo-1$\lambda^6$-isothiazolidin-5-ylmethyl]-amide,
5-Chloro-thiophene-2-carboxylic acid {2-[[5-(5-chloro-thiophen-2-yl)-isoxazol-3-ylmethyl]-(1-isopropyl-piperidin-4-yl)-sulfamoyl]-ethyl}-amide,
5-Chloro-thiophene-2-carboxylic acid {2-[(5-cyclopropyl-[1,3,4]thiadiazol-2-ylmethyl)-(1-isopropyl-piperidin-4-yl)-sulfamoyl]-ethyl}-amide or
5-Chloro-thiophene-2-carboxylic acid {2-[[(5-chloro-pyridin-2-ylcarbamoyl)-methyl]-(1-isopropyl-piperidin-4-yl)-sulfamoyl]-ethyl}-amide.

3. A pharmaceutical preparation, comprising a compound according to claim 1 and a pharmaceutically acceptable carrier.

\* \* \* \* \*